(12) United States Patent
Bello et al.

(10) Patent No.: US 8,420,372 B2
(45) Date of Patent: Apr. 16, 2013

(54) PORCINE ADENO-ASSOCIATED VIRUSES

(76) Inventors: Alexander Bello, Winnipeg (CA); Michael Gray, Winnipeg (CA); Heinz Feldmann, Hamilton, MT (US); Gary Kobinger, Winnipeg (CA)

( * ) Notice: Subject to any disclaimer, the term of this patent is extended or adjusted under 35 U.S.C. 154(b) by 185 days.

(21) Appl. No.: 12/676,016

(22) PCT Filed: Sep. 4, 2008

(86) PCT No.: PCT/CA2008/001557
§ 371 (c)(1),
(2), (4) Date: Jul. 7, 2010

(87) PCT Pub. No.: WO2009/030025
PCT Pub. Date: Mar. 12, 2009

(65) Prior Publication Data
US 2010/0272685 A1 Oct. 28, 2010

Related U.S. Application Data

(60) Provisional application No. 60/969,733, filed on Sep. 4, 2007.

(51) Int. Cl.
*C12N 7/02* (2006.01)
*C12N 15/86* (2006.01)
*A61K 48/00* (2006.01)

(52) U.S. Cl.
USPC .................. 435/235.1; 424/93.2; 435/320.1

(58) Field of Classification Search ....................... None
See application file for complete search history.

(56) References Cited

U.S. PATENT DOCUMENTS 7,427,396 B2 * 9/2008 Arbetman et al. ........... 424/93.2
2006/0018841 A1 1/2006 Arbetman et al.

OTHER PUBLICATIONS

Bello et al, Isolation and evaluation of novel adeno-associated virus sequences from porcine tissues. Gene Ther. 16(11):1320-13288,2009.*
Arbetman et al., "Novel Caprine Adeno-Associated Virus (AAV) Capsid (AAV-Go.1) Is Closely Related to the Primate AAV-5 and Has Unique Tropism and Neutralization Properties", Journal of Virology, Dec. 2005, vol. 79, p. 15239, Figure 1 and p. 15240.

* cited by examiner

*Primary Examiner* — Michael Burkhart
(74) *Attorney, Agent, or Firm* — Michael R. Williams; Ade & Company Inc

(57) ABSTRACT

Porcine tissues were screened for the presence of Adeno-Associated Viruses (AAV). Several AAV sequences were isolated from various porcine tissues, and BLAST analysis confirmed high to low homology with known AAV sequences of different origin. Sequence analysis confirmed the isolation of at least three novel porcine AAV isolates which we named AAVpo1, -po2, and -po3. Novel AAVs derived from porcine tissues may significantly contribute to the generation of new preventive or curative clinical modalities acceptable for human use.

2 Claims, 9 Drawing Sheets

Figure 3:
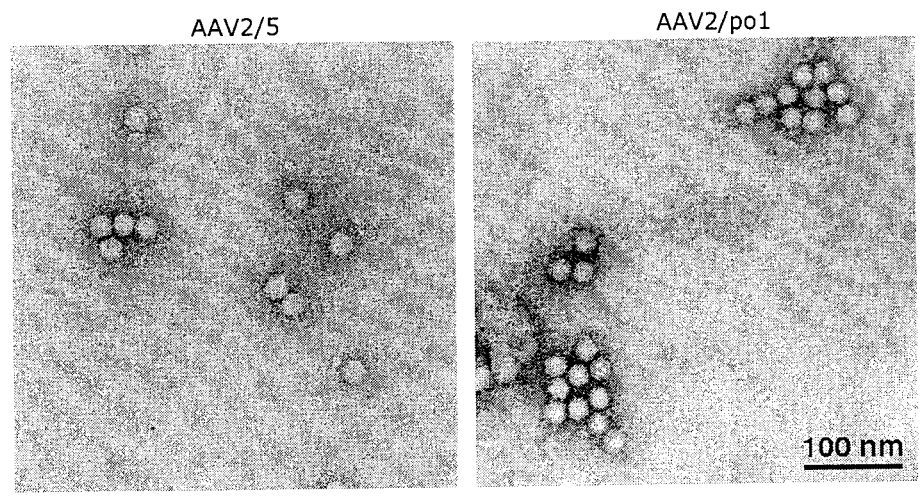

Figure 1.
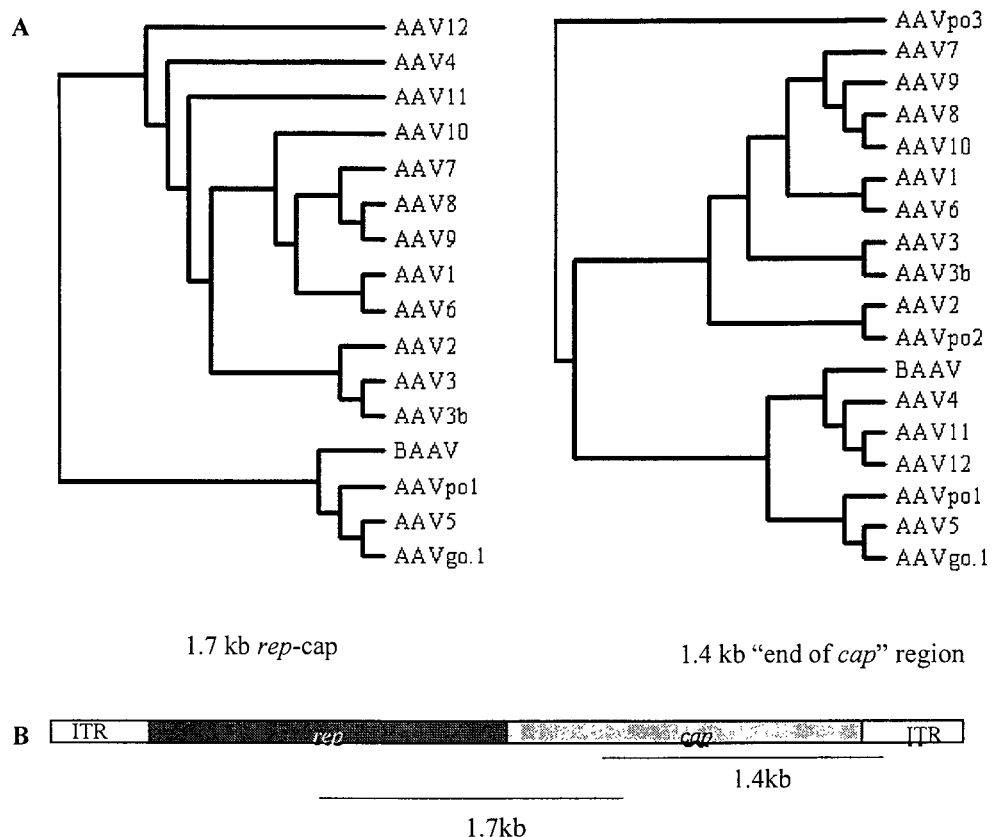
1.7 kb *rep*-cap
1.4 kb "end of *cap*" region
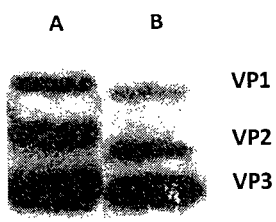
Figure 2.

AAVpo1a Rep/Cap 1643 bp (SEQ ID No. 18)

GGTGCGTAAACTGGACCAATGAGAACTTTCCCTTCAACGACTGCGTGGACAA
GATGCTCATCTGGTGGGAGGAGGGCAAGATGACCAACAAGGTGGTCGAGTCC
GCCAAGGCCATCCTGGGCGGCTCCCGTGTGAGAGTGGACCAGAAGTGTAAGT
CTTCTGCCCAGATAGACGCCACCCCGGTCATCGTCACCTCCAACACCAACAT
GTGTATCGTGGTGGACGGAAACTCGACGACGTTCGAACATCAGCAGCCGCTG
GAGGACCGAATGTTCAAGTTTGAGCTGACGAAGCGGCTCCCGCCGGACTTTG
GCAAGATCACCAAGAGGGAGGTCAAAGACTTTTTTGCCTGGGCTGAGGCCAA
TCTGGTGCCGGTGACTCATGAGTTTCGGGTTCCCAAGGGGGCGGAGAAATCT
CTGAAACGCCCACTCAGTGACGTCACTGACACTAGCTATAAAAGTCCGGAGA
AGCGGGCGAGGGTCTCATTTGCTCCGGAGACGCCCGACTGTTCGGACGAGAC
CGCCGACCCCGCTCCTCCGCGACCGATCGATTGGACCTCCAGGTATGATTGTC
GATGCGATTCGCATGCTCGCGTCGAGACTGTTGATGAAATGTGTGAGGAATG
CGAATATCTGAATCGGGGCAAAAACGGTTGTATCCCTCATAAAATGAACTAT
TGTCAAATCTGTCATGATGTACCCCCCTGGCTAAAGGAAAAGTGTCTGATGT
AGTGGATCTTGACGATGCCAATAAAGAGCAGTAAATAAAGCGAGTAGTCATG
TCGTTTGTTGATCACCCTCCAGATTGGCTTGAGGAGATTGGTGAGGGTCTAAA
GGAGTTTTTGGGACTCGAACCTGGCCCACCCAAACCGAAGCCCAACCAGCAG
AAGCAAGACGACGCCCGTGGTCTTGTACTGCCTGGATATAATTACCTGGGAC
CCGGAAACGGTCTCGACCGCGGAGAACCTGTCAACCGGGCTGACGAGGTCGC
GCGAGAGCACGACATCTCGTACAACGAGCAGCTCCAGGCGGGAGACAACCC
CTACCTCAAGTACAACCACGCGGACGCCGAGTTTCAGGAGAAGCTCGCGGAC
GACACCTCCTTCGGGGGCAACCTCGGCAAGGCAGTCTTTCAGGCCAAAAAAA
GGGTTCTCGAACCTTTTGGCCTGGTTGAGGAGCCTGTTAAGACGGCTGCTAAA
GGCGAGCGGATAGACGACCACTATCCCAAAAAGAAGAAGGCTCGGATCGAA
GAGACCGAAGCTGGAACCAGCGGAGCCCAGCAGCTGCAGATCCCAGCCCAA
CCAGCCTCAAGTTTGGGAGCTGATACAATGTCTGCGGGAGGTGGCAGCCCAC
TGGGCGACAATAACCAAGGCGCCGATGGAGTGGGCAATGCCTCGGGAGATT
GGCATTGCGATTCCACGTGGATGGGGGACCGAGTCATCACCAAGTCCACCCG
AACCTGGGTGCTGCCCAGCTACAACAACCATCAGTACCTTGAGATCCACAGC
GGTTCCGTCGACGGAAGCAACGCTAACGCTTATTTGGATACAGCACCCCCT
GGGGGTACTTTGACTTCAACCGCTTCCACAGCCACTGGAGCCCCCGAGACTG
GCAGCGACTCATCAACAACAACTGGGGATTC

Figure 6

AAVpo1b End of Cap 1398 bp (SEQ ID No. 19)

GACTTCAACCGCTTCCACAGCCACTGGAGCCCCCGAGACTGGCAGCGACTCG
TCAACAACTACTGGGGATTCAGACCCCGGTCCCTCAAGGTCAAGATCTTTAA
CATCCAAGTCAAGGAAGTCACGACGCAGGACGGCACCACCACCATCGCCAA
CAACCTCACCTCCACCGTCCAAGTGTTTACGGACAACGACTACCAGCTACCG
TACGTCATCGGCAACGGAACGGAGGGGTGCCTGCCGGCCTTCCCTCCGCAGG
TCTTTACGCTGCCGCAGTACGGCTACGCGACACTGAACCGTAACAACACCGA
CGATCCCACCGAGCGGAGCAGTTTCTTCTGCCTGGAATACTTTCCCAGCAAG
ATGCTGCGGACGGGCAACAACTTTGAATTCACCTACAGCTTCGAGGAGGTGC
CCTTCCACTGCAGCTTCGCTCCCAGCCAGAACCTCTTCAAGCTGGCCAATCCG
CTGGTGGACCAGTACCTGTACCGCTTTGTGAGCACCGACACTTCCGGTAACCT
ACAGTTCCAAAAGAACCTGAAGGCCAGATATGCCAACACTTACAAGAATTGG
TTTCCGGGGCCCATGTGCCGGACCCAGGGCTGGTACACAAGCGCGGGCACAT
ATAACAACAAAGGCGTTGCCAACTTTGATACTTCAAACAAGATGGAACTGGA
GGGGGCTAGTTACCAAGTAAACCCTCAACCAAATGGAATGACAAACACGCTT
CAGGATAGTAACAAATACGCGCTTGAAAACACCATGATCTTCAACGCACAGA
ACGCCCCTCCGGGAACGACCTCTCTGTACCAGGAGAACAATCTTTTGATAAC
CAGCGAGAGCGAGACGCAGCCTGTGAACCGATTGGCCTACAACACCGGTGGT
CAGGTATCAAACAACAACCAGAATTCAAATACACATCCTACGGTCGGAGTAT
ACAATCACCAGGAAGTGTTGCCTGGTAGCGTGTGGATGGACAGAGACGTATA
CCTTCAGGGCCCCATCTGGGCCAAAATCCCGGAGACAGGGGCACACTTTCAT
CCTTCTCCGGCTATGGGCGGATTCGGACTCAAACACCCACCGCCCATGATGCT
CATCAAGAACACACCGGTACCTAGCAACGTCGCTGCCTTCTCTGACGTGCCC
GTTAAAAGCTTCATCACCCAGTACAGCACCGGACAGGTCACGGTGGAGATTG
AATGGGAGCTCAAGAAAGAAACTCCAAGAGGTGGAATCCCGAGATACAGT
ACACCAACAACTACAACAACCCTACATTCGTGGACTTTGCTCCAGACACCTC
CGGCGAGTACAGGACTACGGGGGCTATTGGAACCCGTTACCTTACCCGACCC
CTGTAACCCTATCCTGTCACATGTTTCAATAAACCGGGTCATTC

Figure 7

AAVpo1c Full Cap 2151 bp (SEQ ID No. 20)
ATGTCGTTTGTTGATCACCCTCCAGATTGGCTTGAGGAGATTGGTGAGGGTCT
AAAGGAGTTTTTGGGACTCGAACCTGGCCCACCCAAACCGAAGCCCAACCAG
CAGAAGCAAGACGACGCCCGTGGTCTTGTACTGCCTGGATATAATTACCTGG
GACCCGGAAACGGTCTCGACCGCGGAGAACCTGTCAACCGGGCTGACGAGG
TCGCGCGAGAGCACGACATCTCGTACAACGAGCAGCTCCAGGCGGGAGACA
ACCCCTACCTCAAGTACAACCACGCGGACGCCGAGTTTCAGGAGAAGCTCGC
GGACGACACCTCCTTCGGGGGCAACCTCGGCAAGGCAGTCTTTCAGGCCAAA
AAAGGGTTCTCGAACCTTTTGGCCTGGTTGAGGAGCCTGTTAAGACGGCTG
CTAAAGGCGAGCGGATAGACGACCACTATCCCAAAAAGAAGAAGGCTCGGA
TCGAAGAGACCGAAGCTGGAACCAGCGGAGCCCAGCAGCTGCAGATCCCAG
CCCAACCAGCCTCAAGTTTGGGAGCTGATACAATGTCTGCGGGAGGTGGCAG
CCCACTGGGCGACAATAACCAAGGCGCCGATGGAGTGGGCAATGCCTCGGG
AGATTGGCATTGCGATTCCACGTGGATGGGGGACCGAGTCATCACCAAGTCC
ACCCGAACCTGGGTGCTGCCCAGCTACAACAACCATCAGTACCTTGAGATCC
ACAGCGGTTCCGTCGACGGAAGCAACGCTAACGCTTATTTTGGATACAGCAC
CCCCTGGGGGTACTTTGACTTCAACCGCTTCCACAGCCACTGGAGCCCCCGA
GACTGGCAGCGACTCGTCAACAACTACTGGGGATTCAGACCCCGGTCCCTCA
AGGTCAAGATCTTTAACATCCAAGTCAAGGAAGTCACGACGCAGGACGGCAC
CACCACCATCGCCAACAACCTCACCTCCACCGTCCAAGTGTTTACGGACAAC
GACTACCAGCTACCGTACGTCATCGGCAACGGAACGGAGGGGTGCCTGCCGG
CCTTCCCTCCGCAGGTCTTTACGCTGCCGCAGTACGGCTACGCGACACTGAAC
CGTAACAACACCGACGATCCCACCGAGCGGAGCAGTTTCTTCTGCCTGGAAT
ACTTTCCCAGCAAGATGCTGCGGACGGGCAACAACTTTGAATTCACCTACAG
CTTCGAGGAGGTGCCCTTCCACTGCAGCTTCGCTCCCAGCCAGAACCTCTTCA
AGCTGGCCAATCCGCTGGTGGACCAGTACCTGTACCGCTTTGTGAGCACCGA
CACTTCCGGTAACCTACAGTTCCAAAAGAACTTGAAGGCCAGATATGCCAAC
ACTTACAAGAATTGGTTTCCGGGGCCCATGTGCCGGACCCAGGGCTGGTACA
CAAGCGCGGGCACATATAACAACAAGGCGTTGCCAACTTTGATACTTCAAA
CAAGATGGAACTGGAGGGGGCTAGTTACCAAGTAAACCCTCAACCAAATGG
AATGACAAACACGCTTCAGGATAGTAACAAATACGCGCTTGAAAACACCATG
ATCTTCAACGCACAGAACGCCCCTCCGGGAACGACCTCTCTGTACCAGGAGA
ACAATCTTTTGATAACCAGCGAGAGCGAGACGCAGCCTGTGAACCGATTGGC
CTACAACACCGGTGGTCAGGTATCAAACAACAACCAGAATTCAAATACACAT
CCTACGGTCGGAGTATACAATCACCAGGAAGTGTTGCCTGGTAGCGTGTGGA
TGGACAGAGACGTATACCTTCAGGGCCCCATCTGGGCCAAAATCCCGGAGAC
AGGGGCACACTTTCATCCTTCTCCGGCTATGGGCGGATTCGGACTCAAACAC
CCACCGCCCATGATGCTCATCAAGAACACACCGGTACCTAGCAACGTCGCTG
CCTTCTCTGACGTGCCCGTTAAAAGCTTCATCACCCAGTACAGCACCGGACA
GGTCACGGTGGAGATTGAATGGGAGCTCAAGAAAGAAAACTCCAAGAGGTG
GAATCCCGAGATACAGTACACCAACAACTACAACAACCCTACATTCGTGGAC
TTTGCTCCAGACACCTCCGGCGAGTACAGGACTACGAGGGCTATTGGAACCC
GTTACCTTACCCGACCCCTGTAA

Figure 8

AAVpo2 End of Cap 1385 bp (SEQ ID No. 21)

GACTTCAACCGCTTCCACAGCCACTTCTCGCCGCGAGACTGGCAGCGGCTCA
TCAACAACAACTGGGGGTTCCGGCCCAAGCGACTCAACTTCAAGCTGTTCAA
CATCCAAGTCAAGGAAGTTACGGACACGGACGGCACGAAGACCATCGCCAA
TAACCTTACCAGCACGGTTCAGGTCTTTGCGGATTCGGAGTACCAGCTCCCGT
ACGTCCTCGGATCAGCGCACCAGGGCTGCTTCCCGCCGTTCCCGGCGGACGT
CTTCATGGTCCCGCAGTACGGGTATTTGACGCTGAACAACGGCAGCCAGGCG
ATGGGTCGCTCGTCCTTCTACTGCCTGGAGTACTTTCCGTCGCAGATGCTGCG
GACGGGGAACAACTTCACGTTCAGCTACACCTTCGAGGACGTGCCCTTCCAC
AGCAGCTACGCGCACAGCCAGAGTCTGGACCGGCTCATGAACCCACTCATCG
ACCAGTACCTGTACTACCTAAGCAAGACAAATGACGGTCTAGGATTTTCCCA
AGCGGGACCCAACAGCATGCGCGACCAGTCCAGGAATTGGCTGCCGGGACC
CTGCTTCAGACAACAACGGATTTCAACTGTACCTACACAAAATAACAACGGA
GACTTTTCGTGGACGGGAGCCACAAAGTATCATCTCAATGGAAGAAACTCAG
CAATGAATCCCGGCCCGGCCATGGCCAGCCACAAAGACGACGAACACAGAT
TCTTCCCTCAGAACGGTGTGCTCATCTTTGGAAAACAGGGCGCAGACAAGAC
AAATGCGATACTAGAAAAAGTGATCGTTACAGACGAAGAGGAGATTAGGAC
AACAAATCCTGTAGCCACGGAAGAGTATGGGTTTGTCGCCACTAATCTACAA
AGCTCGGCAGAAACAGCCGAGACCGAAAGAGTCAACGCGCAAGGCATCCTC
CCTGGCATGGTGTGGCAAGACCGAGATGTGTATCTGCAGGGGCCCATCTGGG
CCAAGATCCCCCACACCGACGGACACTTCCACCCCTCACCACTCATGGGAGG
ATTCGGCCTCAAGCACCCGCCTCCGCAGATCCTCATCAAGAACACGCCTGTG
CCTTCGAATCCTCCAGAGACGTTCAACCCGGAAAAGCTCAATTCTTTCATAAC
TCAATATTCTACGGGCCAGGTCAGCGTGGAGATCGAGTGGGAGCTGCAGAAG
GAGAACAGCAAGCGCTGAAACCCCGAGGTCCAGTACACGTCCAACTACAAC
AAGTCTGTTAATGTGGACTTCACCGTGGACACCAACGGTGTGTACTCGGAAC
CGCGCACCATCGGCACCCGATACCTTACCCGCAACCTGTAACCCTACCCTGTC
ACGTGTTCTCAATAAACCGGGTGATTCGTTTCAGT

AAVpo3a Signature Sequence 252 bp (SEQ ID No. 22)

GGTAATTCCTCGGGAAATTGGCATTGCGATTCCACATGGCTGGACAAGCGAG
TCATTACCAAGTCCACCCGAACCTGGAGCCTGCCCACCTACAACAACCACCT
CTACAACAAAATCACCTCCACCGCAGCAAATGGAGACGGAACCTGGTTCGGA
TTCAGCACTCCATGGGGATACTTTGACTTCAACCGCTTCCACTGCCATTTCTC
ACCCCGAGACTGGCAGCGACTCATCAACAACAACTGGGGATTC

Figure 9

AAVpo3b End of Cap 1549 bp (SEQ ID No. 23)

GCGATTCCACATGGCTGGACAAGCGAGTCATTACCAAGTCCACCCGAACCTG
GAGCCTGCCCACCTACAACAACCACCTCTACAACAAAATCACCTCCACCGCA
GCAAATGGAGACGGAACCTGGTTCGGATTCAGCACTCCATGGGGATACTTTG
ACTTCAACCGCTTCCACTGCCATTTCTCACCCCGAGACTGGCAGCGACTCATC
AACAACAACTGGGGCATCCGGCCCAAGAAAATGCACGTCAAACTCTTCAATA
TCCAAGTCAAGGAAGTCACGACGCAAGACTCGACGACGACCATCACCAATA
ACCTTACCAGCACGATTCAGGTGTTTGCGGACACGGAGTACCAGCTGCCGTA
CGTAGCCAGCAACGCCCACGAGGGCTGCCTCCCGCCCTTTCCGGCGGACGTC
TTCATGCTTCCGCAGTATGGCTACTGCACGCTGCAACGCGAGAACTCCAACG
ATCCCGTGGCCCAAAGCTCGTTCTACTGCCTGGAGTACTTCCCCAGTCAGATG
CTGGGGACCGGAAACAACTACTCCATCAGCTACACGTTCGAAGACGTACCCT
TCCACAGCATGTACATGCACAATCAGAGCCTGGACCGGCTGATGAACCCGCT
CATCGACCAGTACCTGTGGTTCCTCAATAATACCGTAGCCACCAACAACACC
AACACCTTCACCAAGTCGACCAAAGACGATTTGCCACGCCAGAATCGCAATT
GGCTACCCGGACCCGCCTTCCAGACGGCGGCCTTCAACTTGAACGGTCAGAA
CCATTTTTTCACGTCCAATCACTGGGGTTTAGTTAACAAGTACTTGATGAATG
GAAGAAACGTGGCGATTGGCCCTGGCCCTGTCGTAGCCCCCAAAAGCACGAC
CTTCCAGGCCGACGGCATGATCTTCGCCAAAAGCGCAGCTACGGCGACATCT
GCTGCCGCTCAAGATACGGTCAACATCACCAGCGAGTCGGAGACGTCCACCG
TCAACCCCATGATGGGCACCAACCCTCTCATTATCAATTCGAGTAATACTCCA
TCTACTTCCGCCCCCACGATGTCGAATCAAGCCGTCAATCCCATCATGCCTGG
CTCCGTTTGGCAAGACAGAGACATCTATCTTCAGGGCCCGATCTGGGCCAAG
ATTCCGCGCACCGATGGAACCTTCCACCCCTCGCCTCTGATGGGAGGTTTCGG
GCTGCGTCATCCTCCTCCACAAATCTTCATCAAGAACACACCCGTTCCGGCCA
ACCCTCCAACCACGTTCAATCCCGCCAAAATCAACGCCTTCATCACCCAATAC
TCGACTGGACAGGTCACCGTCGAGATGGAATGGGAGCTCGAGAAGGAAAAC
AGCAAGCGATGGAACCCGGAAATCCAGTTCACCAACAACTTCCAGGTTTCGG
ACGGGAACATGGTTCCCTTCTGCGTGGACTCAAATGGCGTCTACTCCGAACC
ACGCCCCATCGGAACCCGCTACCTCACCCGAACCCTCTAACCCTATCTTGTCG
CATATCCTCAATAAACCGGGTTATTCGTGTCAGT

Figure 10

AAVpo1 VP1 Peptide (SEQ ID No. 24)
MSFVDHPPDWLEEIGEGLKEFLGLEPGPPKPKPNQQKQDDARGLVLPGYNYLGP
GNGLDRGEPVNRADEVAREHDISYNEQLQAGDNPYLKYNHADAEFQEKLADDT
SFGGNLGKAVFQAKKRVLEPFGLVEEPVKTAAKGERIDDHYPKKKKARIEETEA
GTSGAQQLQIPAQPASSLGADTMSAGGGSPLGDNNQGADGVGNASGDWHCDST
WMGDRVITKSTRTWVLPSYNNHQYLEIHSGSVDGSNANAYFGYSTPWGYFDFN
RFHSHWSPRDWQRLVNNYWGFRPRSLKVKIFNIQVKEVTTQDGTTTIANNLTST
VQVFTDNDYQLPYVIGNGTEGCLPAFPPQVFTLPQYGYATLNRNNTDDPTERSSF
FCLEYFPSKMLRTGNNFEFTYSFEEVPFHCSFAPSQNLFKLANPLVDQYLYRFVST
DTSGNLQFQKNLKARYANTYKNWFPGPMCRTQGWYTSAGTYNNKGVANFDTS
NKMELEGASYQVNPQPNGMTNTLQDSNKYALENTMIFNAQNAPPGTTSLYQEN
NLLITSESETQPVNRLAYNTGGQVSNNNQNSNTHPTVGVYNHQEVLPGSVWMD
RDVYLQGPIWAKIPETGAHFHPSPAMGGFGLKHPPPMMLIKNTPVPSNVAAFSD
VPVKSFITQYSTGQVTVEIEWELKKENSKRWNPEIQYTNNYNNPTFVDFAPDTSG
EYRTTRAIGTRYLTRPL

AAVpo1 VP2 Peptide (SEQ ID No. 25)
TAAKGERIDDHYPKKKKARIEETEAGTSGAQQLQIPAQPASSLGADTMSAGGGS
PLGDNNQGADGVGNASGDWHCDSTWMGDRVITKSTRTWVLPSYNNHQYLEIH
SGSVDGSNANAYFGYSTPWGYFDFNRFHSHWSPRDWQRLVNNYWGFRPRSLK
VKIFNIQVKEVTTQDGTTTIANNLTSTVQVFTDNDYQLPYVIGNGTEGCLPAFPPQ
VFTLPQYGYATLNRNNTDDPTERSSFFCLEYFPSKMLRTGNNFEFTYSFEEVPFH
CSFAPSQNLFKLANPLVDQYLYRFVSTDTSGNLQFQKNLKARYANTYKNWFPGP
MCRTQGWYTSAGTYNNKGVANFDTSNKMELEGASYQVNPQPNGMTNTLQDSN
KYALENTMIFNAQNAPPGTTSLYQENNLLITSESETQPVNRLAYNTGGQVSNNN
QNSNTHPTVGVYNHQEVLPGSVWMDRDVYLQGPIWAKIPETGAHFHPSPAMGG
FGLKHPPPMMLIKNTPVPSNVAAFSDVPVKSFITQYSTGQVTVEIEWELKKENSK
RWNPEIQYTNNYNNPTFVDFAPDTSGEYRTTRAIGTRYLTRPL

AAVpo1 VP3 Peptide (SEQ ID No. 26)
MGDRVITKSTRTWVLPSYNNHQYLEIHSGSVDGSNANAYFGYSTPWGYFDFNRF
HSHWSPRDWQRLVNNYWGFRPRSLKVKIFNIQVKEVTTQDGTTTIANNLTSTVQ
VFTDNDYQLPYVIGNGTEGCLPAFPPQVFTLPQYGYATLNRNNTDDPTERSSFFC
LEYFPSKMLRTGNNFEFTYSFEEVPFHCSFAPSQNLFKLANPLVDQYLYRFVSTD
TSGNLQFQKNLKARYANTYKNWFPGPMCRTQGWYTSAGTYNNKGVANFDTSN
KMELEGASYQVNPQPNGMTNTLQDSNKYALENTMIFNAQNAPPGTTSLYQENN
LLITSESETQPVNRLAYNTGGQVSNNNQNSNTHPTVGVYNHQEVLPGSVWMDR
DVYLQGPIWAKIPETGAHFHPSPAMGGFGLKHPPPMMLIKNTPVPSNVAAFSDVP
VKSFITQYSTGQVTVEIEWELKKENSKRWNPEIQYTNNYNNPTFVDFAPDTSGEY
RTTRAIGTRYLTRPL

Figure 11

SEQUENCE LISTING

<160> NUMBER OF SEQ ID NOS: 26

<210> SEQ ID NO 1
<211> LENGTH: 26
<212> TYPE: DNA
<213> ORGANISM: artificial sequence
<220> FEATURE:
<223> OTHER INFORMATION: pcr primer

<400> SEQUENCE: 1
ggtgcgtaaa ctggaccaat gagaac                                    26

<210> SEQ ID NO 2
<211> LENGTH: 26
<212> TYPE: DNA
<213> ORGANISM: artificial sequence
<220> FEATURE:
<223> OTHER INFORMATION: pcr primer

<400> SEQUENCE: 2 gaatcccag ttgttgttga tgagtc                                     26

<210> SEQ ID NO 3
<211> LENGTH: 25
<212> TYPE: DNA
<213> ORGANISM: artificial sequence
<220> FEATURE:
<223> OTHER INFORMATION: pcr primer

<400> SEQUENCE: 3
ggtaattcct cgggaaattg gcatt                                     25

<210> SEQ ID NO 4
<211> LENGTH: 22
<212> TYPE: DNA
<213> ORGANISM: artificial sequence
<220> FEATURE:
<223> OTHER INFORMATION: pcr primer

<400> SEQUENCE: 4
gactcatcaa caacwactgg gg                                        22

<210> SEQ ID NO 5
<211> LENGTH: 27
<212> TYPE: DNA
<213> ORGANISM: artificial sequence
<220> FEATURE:
<223> OTHER INFORMATION: pcr primer

<400> SEQUENCE: 5
actgamacga athammcggt ttattga                                   27

```
<210> SEQ ID NO 6
<211> LENGTH: 21
<212> TYPE: DNA
<213> ORGANISM: artificial sequence
<220> FEATURE:
<223> OTHER INFORMATION: pcr primer

<400> SEQUENCE: 6
atgtagtgga tcttgacgat g                                           21

<210> SEQ ID NO 7
<211> LENGTH: 20
<212> TYPE: DNA
<213> ORGANISM: artificial sequence
<220> FEATURE:
<223> OTHER INFORMATION: pcr primer

<400> SEQUENCE: 7
catgtgacag gatagggtta                                             20

<210> SEQ ID NO 8
<211> LENGTH: 21
<212> TYPE: DNA
<213> ORGANISM: artificial sequence
<220> FEATURE:
<223> OTHER INFORMATION: pcr primer

<400> SEQUENCE: 8
ggarattggc attgcgattc c                                           21

<210> SEQ ID NO 9
<211> LENGTH: 24
<212> TYPE: DNA
<213> ORGANISM: artificial sequence
<220> FEATURE:
<223> OTHER INFORMATION: pcr primer

<400> SEQUENCE: 9
gacttcaacc gcttccacag ccac                                        24

<210> SEQ ID NO 10
<211> LENGTH: 20
<212> TYPE: DNA
<213> ORGANISM: artificial sequence
<220> FEATURE:
<223> OTHER INFORMATION: pcr primer

<400> SEQUENCE: 10
ttggccactc cctctmgcgc                                             20

<210> SEQ ID NO 11
<211> LENGTH: 20
<212> TYPE: DNA
<213> ORGANISM: artificial sequence
<220> FEATURE:
<223> OTHER INFORMATION: pcr primer

<400> SEQUENCE: 11
acgcasccgt aaaagggcac                                             20

<210> SEQ ID NO 12
<211> LENGTH: 22
<212> TYPE: DNA
<213> ORGANISM: artificial sequence
<220> FEATURE:
<223> OTHER INFORMATION: pcr primer
```

-continued

```
<400> SEQUENCE: 12
tttgsccact ccctctmtgc gc                                              22

<210> SEQ ID NO 13
<211> LENGTH: 19
<212> TYPE: DNA
<213> ORGANISM: artificial sequence
<220> FEATURE:
<223> OTHER INFORMATION: pcr primer

<400> SEQUENCE: 13
cgtggacttt gctccagac                                                  19

<210> SEQ ID NO 14
<211> LENGTH: 20
<212> TYPE: DNA
<213> ORGANISM: artificial sequence
<220> FEATURE:
<223> OTHER INFORMATION: pcr primer

<400> SEQUENCE: 14
cagtctcggg gtgagaaatg                                                 20

<210> SEQ ID NO 15
<211> LENGTH: 24
<212> TYPE: DNA
<213> ORGANISM: artificial sequence
<220> FEATURE:
<223> OTHER INFORMATION: pcr primer

<400> SEQUENCE: 15
ttaacccgcc atgctactta tcta                                            24

<210> SEQ ID NO 16
<211> LENGTH: 25
<212> TYPE: DNA
<213> ORGANISM: artificial sequence
<220> FEATURE:
<223> OTHER INFORMATION: pcr primer

<400> SEQUENCE: 16
tgaactaatg accccgtaat tgatt                                           25

<210> SEQ ID NO 17
<211> LENGTH: 33
<212> TYPE: DNA
<213> ORGANISM: artificial sequence
<220> FEATURE:
<223> OTHER INFORMATION: pcr primer

<400> SEQUENCE: 17
ctctaggaag atcggaattc gcccttaagc tag                                  33

<210> SEQ ID NO 18
<211> LENGTH: 1643
<212> TYPE: DNA
<213> ORGANISM: porcine adeno-associated virus

<400> SEQUENCE: 18
ggtgcgtaaa ctggaccaat gagaactttc ccttcaacga ctgcgtggac aagatgctca     60
tctggtggga ggagggcaag atgaccaaca aggtggtcga gtccgccaag gccatcctgg    120
gcggctcccg tgtgagagtg gaccagaagt gtaagtcttc tgcccagata gacgccaccc    180
cggtcatcgt cacctccaac accaacatgt gtatcgtggt ggacggaaac tcgacgacgt    240
```

```
tcgaacatca gcagccgctg gaggaccgaa tgttcaagtt tgagctgacg aagcggctcc      300
cgccggactt tggcaagatc accaagaggg aggtcaaaga cttttttgcc tgggctgagg      360
ccaatctggt gccggtgact catgagtttc gggttcccaa gggggcggag aaatctctga      420
aacgcccact cagtgacgtc actgacacta gctataaaag tccggagaag cgggcgaggg      480
tctcatttgc tccggagacg cccgactgtt cggacgagac cgccgacccc gctcctccgc      540
gaccgatcga ttggacctcc aggtatgatt gtcgatgcga ttcgcatgct cgcgtcgaga      600
ctgttgatga atgtgtgag gaatgcgaat atctgaatcg gggcaaaaac ggttgtatcc       660
ctcataaaat gaactattgt caaatctgtc atgatgtacc ccctggcta aaggaaaaag       720 tgtctgatgt agtggatctt gacgatgcca ataaagagca gtaaataaag cgagtagtca     780
tgtcgtttgt tgatcaccct ccagattggc ttgaggagat tggtgagggt ctaaaggagt      840
ttttgggact cgaacctggc ccacccaaac cgaagcccaa ccagcagaag caagacgacg      900
cccgtggtct tgtactgcct ggatataatt acctgggacc cggaaacggt ctcgaccgcg      960
gagaacctgt caaccgggct gacgaggtcg cgcgagagca cgacatctcg tacaacgagc     1020
agctccaggc gggagacaac ccctacctca gtacaaccag cgcggacgcc gagtttcagg     1080
agaagctcgc ggacgacacc tccttcgggg gcaacctcgg caaggcagtc tttcaggcca     1140 aaaaagggt tctcgaacct tttggcctgg ttgaggagcc tgttaagacg gctgctaaag      1200
gcgagcggat agacgaccac tatcccaaaa agaagaaggc tcggatcgaa gagaccgaag     1260
ctggaaccag cggagcccag cagctgcaga tcccagccca accagcctca gtttgggag     1320 ctgatacaat gtctgcggga ggtggcagcc cactgggcga cataaccaa ggcgccgatg      1380 gagtgggcaa tgcctcggga gattggcatt gcgattccac gtggatgggg gaccgagtca     1440
tcaccaagtc caccccgaacc tgggtgctgc ccagctacaa caaccatcag taccttgaga     1500 tccacgcgg ttccgtcgac ggaagcaacg ctaacgctta ttttggatac agcacccct      1560 gggggtactt tgacttcaac cgcttccaca gccactggag cccccgagac tggcagcgac     1620
tcatcaacaa caactgggga ttc                                             1643
```

<210> SEQ ID NO 19
<211> LENGTH: 1398
<212> TYPE: DNA
<213> ORGANISM: porcine adeno-associated virus

<400> SEQUENCE: 19

```
gacttcaacc gcttccacag ccactggagc ccccgagact ggcagcgact cgtcaacaac       60
tactggggat tcagaccccg gtccctcaag gtcaagatct ttaacatcca agtcaaggaa      120
gtcacgacgc aggacggcac caccaccatc gccaacaacc tcacctccac cgtccaagtg     180
tttacggaca acgactacca gctaccgtac gtcatcggca acggaacgga ggggtgcctg     240
ccggccttcc ctccgcaggt cttttacgctg ccgcagtacg gctacgcgac actgaaccgt     300
aacaacaccg acgatcccac cgagcggagc agtttcttct gcctggaata ctttcccagc     360
aagatgctgc ggacgggcaa caactttgaa ttcacctaca gcttcgagga ggtgcccttc     420
cactgcagct tcgctcccag ccagaacctc ttcaagctgg ccaatccgct ggtggaccag     480
tacctgtacc gctttgtgag caccgacact tccgtaacc tacagttcca aaagaacctg     540
aaggccagat atgccaacac ttacaagaat tggtttccgg ggcccatgtg ccggacccag    600
ggctggtaca aagcgcggg cacatataac aacaaggcg ttgccaactt tgatacttca       660
aacaagatgg aactggaggg ggctagttac caagtaaacc ctcaaccaaa tggaatgaca      720
```

-continued

```
aacacgcttc aggatagtaa caaatacgcg cttgaaaaca ccatgatctt caacgcacag    780
aacgcccctc cgggaacgac ctctctgtac caggagaaca atcttttgat aaccagcgag    840
agcgagacgc agcctgtgaa ccgattggcc tacaacaccg gtggtcaggt atcaaacaac    900
aaccagaatt caaatacaca tcctacggtc ggagtataca atcaccagga agtgttgcct    960
ggtagcgtgt ggatggacag agacgtatac cttcagggcc ccatctgggc caaaatcccg   1020
gagacagggg cacactttca tccttctccg gctatgggcg gattcggact caaacaccca   1080
ccgcccatga tgctcatcaa gaacacaccg gtacctagca acgtcgctgc cttctctgac   1140
gtgcccgtta aaagcttcat cacccagtac agcaccggac aggtcacggt ggagattgaa   1200
tgggagctca agaaagaaaa ctccaagagg tggaatcccg agatacagta caccaacaac   1260
tacaacaacc ctacattcgt ggactttgct ccagacacct ccggcgagta caggactacg   1320
ggggctattg gaacccgtta ccttacccga cccctgtaac cctatcctgt cacatgtttt   1380
caataaaccg ggtcattc                                                 1398

<210> SEQ ID NO 20
<211> LENGTH: 2151
<212> TYPE: DNA
<213> ORGANISM: porcine adeno-associated virus

<400> SEQUENCE: 20
atgtcgtttg ttgatcaccc tccagattgg cttgaggaga ttggtgaggg tctaaaggag     60
tttttgggac tcgaacctgg cccacccaaa ccgaagccca accagcagaa gcaagacgac    120
gcccgtggtc ttgtactgcc tggatataat tacctgggac ccggaaacgg tctcgaccgc    180
ggagaacctg tcaaccgggc tgacgaggtc gcgcgagagc acgacatctc gtacaacgag    240
cagctccagg cgggagacaa cccctacctc aagtacaacc acgcggacgc cgagtttcag    300
gagaagctcg cggacgacac ctccttcggg ggcaacctcg gcaaggcagt ctttcaggcc    360
aaaaaaaggg ttctcgaacc ttttggcctg gttgaggagc tgttaagac ggctgctaaa    420
ggcgagcgga tagacgacca ctatcccaaa aagaagaagg ctcggatcga agagaccgaa    480
gctggaacca gcggagccca gcagctgcag atcccagccc aaccagcctc aagtttggga    540
gctgatacaa tgtctgcggg aggtggcagc ccactgggcg acaataacca aggcgccgat    600
ggagtgggca atgcctcggg agattggcat tgcgattcca cgtggatggg ggaccgagtc    660
atcaccaagt ccacccgaac ctgggtgctg cccagctaca caaccatca gtaccttgag    720
atccacagcg gttccgtcga cggaagcaac gctaacgctt attttggata cagcaccccc    780
tgggggtact ttgacttcaa ccgcttccac agccactgga gccccgaga ctggcagcga    840
ctcgtcaaca actactgggg attcagaccc cggtccctca aggtcaagat ctttaacatc    900
caagtcaagg aagtcacgac gcaggacggc accaccacca tcgccaacaa cctcacctcc    960
accgtccaag tgtttacgga caacgactac cagctaccgt acgtcatcgg caacggaacg   1020
gagggggtgc ctgccggcct tcctccgcag gtctttacgc tgccgcagta cggctacgcg   1080
acactgaacc gtaacaacac cgacgatccc accgagcgga gcagtttctt ctgcctggaa   1140
tactttccca gcaagatgct gcggacgggc aacaactttg aattcaccta cagcttcgag   1200
gaggtgcccct tccactgcag cttcgctccc agccagaacc tcttcaagct ggccaatccg   1260
ctggtggacc agtacctgta ccgctttgtg agcaccgaca cttccggtaa cctacagttc   1320
caaaagaact tgaaggccag atatgccaac acttacaaga attggttccc ggggcccatg   1380
tgccggaccc agggctggta cacaagcgcg ggcacatata caacaaagg cgttgccaac   1440
```

-continued

```
tttgatactt caaacaagat ggaactggag ggggctagtt accaagtaaa ccctcaacca      1500
aatggaatga caaacacgct tcaggatagt aacaaatacg cgcttgaaaa caccatgatc      1560
ttcaacgcac agaacgcccc tccgggaacg acctctctgt accaggagaa caatcttttg      1620
ataaccagcg agagcgagac gcagcctgtg aaccgattgg cctacaacac cggtggtcag      1680
gtatcaaaca caaccagaa ttcaaataca catcctacgg tcggagtata caatcaccag       1740
gaagtgttgc ctggtagcgt gtggatggac agagacgtat accttcaggg ccccatctgg      1800
gccaaaatcc cggagacagg ggcacacttt catccttctc cggctatggg cggattcgga      1860
ctcaaacacc caccgcccat gatgctcatc aagaacacac cggtacctag caacgtcgct      1920
gccttctctg acgtgcccgt taaaagcttc atcacccagt acagcaccgg acaggtcacg      1980
gtggagattg aatgggagct caagaaagaa aactccaaga ggtggaatcc cgagatacag      2040
tacaccaaca actacaacaa ccctacattc gtggactttg ctccagacac ctccggcgag      2100
tacaggacta cgagggctat tggaacccgt taccttaccc gaccccctgta a             2151

<210> SEQ ID NO 21
<211> LENGTH: 1385
<212> TYPE: DNA
<213> ORGANISM: porcine adeno-associated virus

<400> SEQUENCE: 21
gacttcaacc gcttccacag ccacttctcg ccgcgagact ggcagcggct catcaacaac       60 aactggggt tccggcccaa gcgactcaac ttcaagctgt tcaacatcca agtcaaggaa       120
gttacggaca cggacggcac gaagaccatc gccaataacc ttaccagcac ggttcaggtc      180
tttgcggatt cggagtacca gctcccgtac gtcctcggat cagcgcacca gggctgcttc      240
ccgccgttcc cggcggacgt cttcatggtc ccgcagtacg gtatttgac gctgaacaac      300 ggcagccagg cgatgggtcg ctcgtccttc tactgcctgg agtactttcc gtcgcagatg      360
ctgcggacgg ggaacaactt cacgttcagc tacaccttcg aggacgtgcc cttccacagc      420
agctacgcgc acagccagag tctggaccgg ctcatgaacc cactcatcga ccagtacctg      480
tactacctaa gcaagacaaa tgacggtcta ggattttccc aagcgggacc caacagcatg      540
cgcgaccagt ccaggaattg gctgccggga ccctgcttca gacaacaacg gatttcaact      600
gtacctacac aaaataacaa cggagacttt cgtggacgg gagccacaaa gtatcatctc      660
aatggaagaa actcagcaat gaatcccggc ccggccatgg ccagccacaa agacgacgaa      720
cacagattct tccctcagaa cggtgtgctc atctttggaa acagggcgc agacaagaca      780 aatgcgatac tagaaaaagt gatcgttaca gacgaagagg agattaggac aacaaatcct      840
gtagccacga aagagtatgg gttttgtcgcc actaatctac aaagctcggc agaaacagcc      900
gagaccgaaa gagtcaacgc gcaaggcatc ctccctggca tggtgtggca agaccgagat      960
gtgtatctgc agggggcccat ctgggccaag atcccccaca ccgacggaca cttccacccc     1020
tcaccactca tgggaggatt cggcctcaag caccccgcctc cgcagatcct catcaagaac     1080
acgcctgtgc cttcgaatcc tccagagacg ttcaacccgg aaaagctcaa ttctttcata     1140
actcaatatt ctacgggcca ggtcagcgtg gagatcgagt gggagctgca aaggagaac      1200 agcaagcgct gaaaccccga ggtccagtac acgtccaact acaacaagtc tgttaatgtg     1260
gacttcaccg tggacaccaa cggtgtgtac tcggaaccgc gcaccatcgg caccccgatac     1320 cttacccgca acctgtaacc ctaccctgtc acgtgttctc aataaaccgg gtgattcgtt     1380
tcagt                                                                 1385
```

<210> SEQ ID NO 22
<211> LENGTH: 252
<212> TYPE: DNA
<213> ORGANISM: porcine adeno-associated virus

<400> SEQUENCE: 22

```
ggtaattcct cgggaaattg gcattgcgat tccacatggc tggacaagcg agtcattacc      60
aagtccaccc gaacctggag cctgccacc tacaacaacc acctctacaa caaaatcacc      120
tccaccgcag caaatggaga cggaacctgg ttcggattca gcactccatg gggatacttt      180
gacttcaacc gcttccactg ccatttctca ccccgagact ggcagcgact catcaacaac      240
aactggggat tc                                                         252
```

<210> SEQ ID NO 23
<211> LENGTH: 1549
<212> TYPE: DNA
<213> ORGANISM: porcine adeno-associated virus

<400> SEQUENCE: 23

```
gcgattccac atggctggac aagcgagtca ttaccaagtc cacccgaacc tggagcctgc      60
ccacctacaa caaccacctc tacaacaaaa tcacctccac cgcagcaaat ggagacggaa      120
cctggttcgg attcagcact ccatggggat actttgactt caaccgcttc cactgccatt      180
tctcaccccg agactggcag cgactcatca acaacaactg gggcatccgg cccaagaaaa      240
tgcacgtcaa actcttcaat atccaagtca aggaagtcac gacgcaagac tcgacgacga      300
ccatcaccaa taaccttacc agcacgattc aggtgtttgc ggacacggag taccagctgc      360
cgtacgtagc cagcaacgcc cacgagggct gcctcccgcc ctttccggcg gacgtcttca      420
tgcttccgca gtatggctac tgcacgctgc aacgcgagaa ctccaacgat cccgtggccc      480
aaagctcgtt ctactgcctg gagtacttcc ccagtcagat gctggggacc ggaaacaact      540
actccatcag ctacacgttc gaagacgtac ccttccacag catgtacatg cacaatcaga      600
gcctggaccg gctgatgaac ccgctcatcg accagtacct gtggttcctc aataataccg      660
tagccaccaa caacaccaac accttcacca gtcgaccaa agacgatttg ccacgccaga      720
atcgcaattg gctacccgga cccgccttcc agacggcggc cttcaacttg aacggtcaga      780
accatttttt cacgtccaat cactgggggtt tagttaacaa gtacttgatg aatggaagaa      840
acgtggcgat tggcccctggc cctgtcgtag ccccaaaag cacgaccttc caggccgacg      900
gcatgatctt cgccaaaagc gcagctacgg cgacatctgc tgccgctcaa gatacggtca      960
acatcaccag cgagtcggag acgtccaccg tcaaccccat gatgggcacc aaccctctca     1020
ttatcaattc gagtaatact ccatctactt ccgcccccac gatgtcgaat caagccgtca     1080
atcccatcat gcctggctcc gtttggcaag acagagacat ctatcttcag ggcccgatct     1140
gggccaagat tccgcgcacc gatggaacct tccacccctc gcctctgatg ggaggtttcg     1200
ggctgcgtca tcctcctcca caaatcttca tcaagaacac acccgttccg gccaaccctc     1260
caaccacgtt caatcccgcc aaaatcaacg ccttcatcac caatactcg actggacagg     1320 tcaccgtcga gatggaatgg gagctcgaga aggaaaacag caagcgatgg aacccggaaa     1380
tccagttcac caacaacttc caggtttcgg acgggaacat ggttcccttc tgcgtggact     1440
caaatggcgt ctactccgaa ccacgcccca tcggaacccg ctacctcacc gaaccctct     1500 aaccctatct tgtcgcatat cctcaataaa ccgggttatt cgtgtcagt              1549
```

<210> SEQ ID NO 24

```
<211> LENGTH: 716
<212> TYPE: PRT
<213> ORGANISM: porcine adeno-associated virus

<400> SEQUENCE: 24

Met Ser Phe Val Asp His Pro Pro Asp Trp Leu Glu Glu Ile Gly Glu
1               5                   10                  15

Gly Leu Lys Glu Phe Leu Gly Leu Glu Pro Gly Pro Lys Pro Lys
            20                  25                  30

Pro Asn Gln Gln Lys Gln Asp Asp Ala Arg Gly Leu Val Leu Pro Gly
            35                  40                  45

Tyr Asn Tyr Leu Gly Pro Gly Asn Gly Leu Asp Arg Gly Glu Pro Val
50                  55                  60

Asn Arg Ala Asp Glu Val Ala Arg Glu His Asp Ile Ser Tyr Asn Glu
65                  70                  75                  80

Gln Leu Gln Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Pro Val Lys Thr Ala Ala Lys Gly Glu Arg Ile
130                 135                 140

Asp Asp His Tyr Pro Lys Lys Lys Ala Arg Ile Glu Glu Thr Glu
145                 150                 155                 160

Ala Gly Thr Ser Gly Ala Gln Gln Leu Gln Ile Pro Ala Gln Pro Ala
                165                 170                 175

Ser Ser Leu Gly Ala Asp Thr Met Ser Ala Gly Gly Gly Ser Pro Leu
            180                 185                 190

Gly Asp Asn Asn Gln Gly Ala Asp Gly Val Gly Asn Ala Ser Gly Asp
        195                 200                 205

Trp His Cys Asp Ser Thr Trp Met Gly Asp Arg Val Ile Thr Lys Ser
210                 215                 220

Thr Arg Thr Trp Val Leu Pro Ser Tyr Asn Asn His Gln Tyr Leu Glu
225                 230                 235                 240

Ile His Ser Gly Ser Val Asp Gly Ser Asn Ala Asn Ala Tyr Phe Gly
                245                 250                 255

Tyr Ser Thr Pro Trp Gly Tyr Phe Asp Phe Asn Arg Phe His Ser His
            260                 265                 270

Trp Ser Pro Arg Asp Trp Gln Arg Leu Val Asn Asn Tyr Trp Gly Phe
        275                 280                 285

Arg Pro Arg Ser Leu Lys Val Lys Ile Phe Asn Ile Gln Val Lys Glu
290                 295                 300

Val Thr Thr Gln Asp Gly Thr Thr Thr Ile Ala Asn Asn Leu Thr Ser
305                 310                 315                 320

Thr Val Gln Val Phe Thr Asp Asn Asp Tyr Gln Leu Pro Tyr Val Ile
                325                 330                 335

Gly Asn Gly Thr Glu Gly Cys Leu Pro Ala Phe Pro Pro Gln Val Phe
            340                 345                 350

Thr Leu Pro Gln Tyr Gly Tyr Ala Thr Leu Asn Arg Asn Asn Thr Asp
        355                 360                 365

Asp Pro Thr Glu Arg Ser Ser Phe Phe Cys Leu Glu Tyr Phe Pro Ser
370                 375                 380

Lys Met Leu Arg Thr Gly Asn Asn Phe Glu Phe Thr Tyr Ser Phe Glu
385                 390                 395                 400
```

```
Glu Val Pro Phe His Cys Ser Phe Ala Pro Ser Gln Asn Leu Phe Lys
            405                 410                 415

Leu Ala Asn Pro Leu Val Asp Gln Tyr Leu Tyr Arg Phe Val Ser Thr
        420                 425                 430

Asp Thr Ser Gly Asn Leu Gln Phe Gln Lys Asn Leu Lys Ala Arg Tyr
    435                 440                 445

Ala Asn Thr Tyr Lys Asn Trp Phe Pro Gly Pro Met Cys Arg Thr Gln
450                 455                 460

Gly Trp Tyr Thr Ser Ala Gly Thr Tyr Asn Asn Lys Gly Val Ala Asn
465                 470                 475                 480

Phe Asp Thr Ser Asn Lys Met Glu Leu Glu Gly Ala Ser Tyr Gln Val
                485                 490                 495

Asn Pro Gln Pro Asn Gly Met Thr Asn Thr Leu Gln Asp Ser Asn Lys
                500                 505                 510

Tyr Ala Leu Glu Asn Thr Met Ile Phe Asn Ala Gln Asn Ala Pro Pro
            515                 520                 525

Gly Thr Thr Ser Leu Tyr Gln Glu Asn Asn Leu Leu Ile Thr Ser Glu
530                 535                 540

Ser Glu Thr Gln Pro Val Asn Arg Leu Ala Tyr Asn Thr Gly Gly Gln
545                 550                 555                 560

Val Ser Asn Asn Asn Gln Asn Ser Asn Thr His Pro Thr Val Gly Val
                565                 570                 575

Tyr Asn His Gln Glu Val Leu Pro Gly Ser Val Trp Met Asp Arg Asp
            580                 585                 590

Val Tyr Leu Gln Gly Pro Ile Trp Ala Lys Ile Pro Glu Thr Gly Ala
        595                 600                 605

His Phe His Pro Ser Pro Ala Met Gly Gly Phe Gly Leu Lys His Pro
    610                 615                 620

Pro Pro Met Met Leu Ile Lys Asn Thr Pro Val Pro Ser Asn Val Ala
625                 630                 635                 640

Ala Phe Ser Asp Val Pro Val Lys Ser Phe Ile Thr Gln Tyr Ser Thr
                645                 650                 655

Gly Gln Val Thr Val Glu Ile Glu Trp Glu Leu Lys Lys Glu Asn Ser
            660                 665                 670

Lys Arg Trp Asn Pro Glu Ile Gln Tyr Thr Asn Asn Tyr Asn Asn Pro
        675                 680                 685

Thr Phe Val Asp Phe Ala Pro Asp Thr Ser Gly Glu Tyr Arg Thr Thr
    690                 695                 700

Arg Ala Ile Gly Thr Arg Tyr Leu Thr Arg Pro Leu
705                 710                 715

<210> SEQ ID NO 25
<211> LENGTH: 580
<212> TYPE: PRT
<213> ORGANISM: porcine adeno-associated virus

<400> SEQUENCE: 25

Thr Ala Ala Lys Gly Glu Arg Ile Asp Asp His Tyr Pro Lys Lys Lys
1               5                   10                  15

Lys Ala Arg Ile Glu Glu Thr Glu Ala Gly Thr Ser Gly Ala Gln Gln
            20                  25                  30

Leu Gln Ile Pro Ala Gln Pro Ala Ser Ser Leu Gly Ala Asp Thr Met
        35                  40                  45

Ser Ala Gly Gly Gly Ser Pro Leu Gly Asp Asn Asn Gln Gly Ala Asp
    50                  55                  60
```

```
Gly Val Gly Asn Ala Ser Gly Asp Trp His Cys Asp Ser Thr Trp Met
 65                  70                  75                  80

Gly Asp Arg Val Ile Thr Lys Ser Thr Arg Thr Trp Val Leu Pro Ser
                 85                  90                  95

Tyr Asn Asn His Gln Tyr Leu Glu Ile His Ser Gly Ser Val Asp Gly
            100                 105                 110

Ser Asn Ala Asn Ala Tyr Phe Gly Tyr Ser Thr Pro Trp Gly Tyr Phe
        115                 120                 125

Asp Phe Asn Arg Phe His Ser His Trp Ser Pro Arg Asp Trp Gln Arg
    130                 135                 140

Leu Val Asn Asn Tyr Trp Gly Phe Arg Pro Arg Ser Leu Lys Val Lys
145                 150                 155                 160

Ile Phe Asn Ile Gln Val Lys Glu Val Thr Thr Gln Asp Gly Thr Thr
                165                 170                 175

Thr Ile Ala Asn Asn Leu Thr Ser Thr Val Gln Val Phe Thr Asp Asn
            180                 185                 190

Asp Tyr Gln Leu Pro Tyr Val Ile Gly Asn Gly Thr Glu Gly Cys Leu
        195                 200                 205

Pro Ala Phe Pro Pro Gln Val Phe Thr Leu Pro Gln Tyr Gly Tyr Ala
    210                 215                 220

Thr Leu Asn Arg Asn Asn Thr Asp Asp Pro Thr Glu Arg Ser Ser Phe
225                 230                 235                 240

Phe Cys Leu Glu Tyr Phe Pro Ser Lys Met Leu Arg Thr Gly Asn Asn
                245                 250                 255

Phe Glu Phe Thr Tyr Ser Phe Glu Glu Val Pro Phe His Cys Ser Phe
            260                 265                 270

Ala Pro Ser Gln Asn Leu Phe Lys Leu Ala Asn Pro Leu Val Asp Gln
        275                 280                 285

Tyr Leu Tyr Arg Phe Val Ser Thr Asp Thr Ser Gly Asn Leu Gln Phe
    290                 295                 300

Gln Lys Asn Leu Lys Ala Arg Tyr Ala Asn Thr Tyr Lys Asn Trp Phe
305                 310                 315                 320

Pro Gly Pro Met Cys Arg Thr Gln Gly Trp Tyr Thr Ser Ala Gly Thr
                325                 330                 335

Tyr Asn Asn Lys Gly Val Ala Asn Phe Asp Thr Ser Asn Lys Met Glu
            340                 345                 350

Leu Glu Gly Ala Ser Tyr Gln Val Asn Pro Gln Pro Asn Gly Met Thr
        355                 360                 365

Asn Thr Leu Gln Asp Ser Asn Lys Tyr Ala Leu Glu Asn Thr Met Ile
    370                 375                 380

Phe Asn Ala Gln Asn Ala Pro Pro Gly Thr Thr Ser Leu Tyr Gln Glu
385                 390                 395                 400

Asn Asn Leu Leu Ile Thr Ser Glu Ser Glu Thr Gln Pro Val Asn Arg
                405                 410                 415

Leu Ala Tyr Asn Thr Gly Gly Gln Val Ser Asn Asn Gln Asn Ser
            420                 425                 430

Asn Thr His Pro Thr Val Gly Val Tyr Asn His Gln Glu Val Leu Pro
    435                 440                 445

Gly Ser Val Trp Met Asp Arg Asp Val Tyr Leu Gln Gly Pro Ile Trp
    450                 455                 460

Ala Lys Ile Pro Glu Thr Gly Ala His Phe His Pro Ser Pro Ala Met
465                 470                 475                 480

Gly Gly Phe Gly Leu Lys His Pro Pro Pro Met Met Leu Ile Lys Asn
```

-continued

```
                 485                 490                 495
Thr Pro Val Pro Ser Asn Val Ala Ala Phe Ser Asp Val Pro Val Lys
            500                 505                 510
Ser Phe Ile Thr Gln Tyr Ser Thr Gly Gln Val Thr Val Glu Ile Glu
            515                 520                 525
Trp Glu Leu Lys Lys Glu Asn Ser Lys Arg Trp Asn Pro Glu Ile Gln
            530                 535                 540
Tyr Thr Asn Asn Tyr Asn Asn Pro Thr Phe Val Asp Phe Ala Pro Asp
545                 550                 555                 560
Thr Ser Gly Glu Tyr Arg Thr Thr Arg Ala Ile Gly Thr Arg Tyr Leu
                565                 570                 575
Thr Arg Pro Leu
            580

<210> SEQ ID NO 26
<211> LENGTH: 501
<212> TYPE: PRT
<213> ORGANISM: porcine adeno-associated VP3 peptide

<400> SEQUENCE: 26

Met Gly Asp Arg Val Ile Thr Lys Ser Thr Arg Thr Trp Val Leu Pro
1               5                   10                  15
Ser Tyr Asn Asn His Gln Tyr Leu Glu Ile His Ser Gly Ser Val Asp
            20                  25                  30
Gly Ser Asn Ala Asn Ala Tyr Phe Gly Tyr Ser Thr Pro Trp Gly Tyr
        35                  40                  45
Phe Asp Phe Asn Arg Phe His Ser His Trp Ser Pro Arg Asp Trp Gln
    50                  55                  60
Arg Leu Val Asn Asn Tyr Trp Gly Phe Arg Pro Arg Ser Leu Lys Val
65                  70                  75                  80
Lys Ile Phe Asn Ile Gln Val Lys Glu Val Thr Thr Gln Asp Gly Thr
                85                  90                  95
Thr Thr Ile Ala Asn Asn Leu Thr Ser Thr Val Gln Val Phe Thr Asp
            100                 105                 110
Asn Asp Tyr Gln Leu Pro Tyr Val Ile Gly Asn Gly Thr Glu Gly Cys
        115                 120                 125
Leu Pro Ala Phe Pro Pro Gln Val Phe Thr Leu Pro Gln Tyr Gly Tyr
    130                 135                 140
Ala Thr Leu Asn Arg Asn Asn Thr Asp Asp Pro Thr Glu Arg Ser Ser
145                 150                 155                 160
Phe Phe Cys Leu Glu Tyr Phe Pro Ser Lys Met Leu Arg Thr Gly Asn
                165                 170                 175
Asn Phe Glu Phe Thr Tyr Ser Phe Glu Glu Val Pro Phe His Cys Ser
            180                 185                 190
Phe Ala Pro Ser Gln Asn Leu Phe Lys Leu Ala Asn Pro Leu Val Asp
        195                 200                 205
Gln Tyr Leu Tyr Arg Phe Val Ser Thr Asp Thr Ser Gly Asn Leu Gln
    210                 215                 220
Phe Gln Lys Asn Leu Lys Ala Arg Tyr Ala Asn Thr Tyr Lys Asn Trp
225                 230                 235                 240
Phe Pro Gly Pro Met Cys Arg Thr Gln Gly Trp Tyr Thr Ser Ala Gly
                245                 250                 255
Thr Tyr Asn Asn Lys Gly Val Ala Asn Phe Asp Thr Ser Asn Lys Met
            260                 265                 270
Glu Leu Glu Gly Ala Ser Tyr Gln Val Asn Pro Gln Pro Asn Gly Met
```

```
                275                 280                 285
Thr Asn Thr Leu Gln Asp Ser Asn Lys Tyr Ala Leu Glu Asn Thr Met
        290                 295                 300

Ile Phe Asn Ala Gln Asn Ala Pro Pro Gly Thr Thr Ser Leu Tyr Gln
305                 310                 315                 320

Glu Asn Asn Leu Leu Ile Thr Ser Glu Ser Glu Thr Gln Pro Val Asn
                325                 330                 335

Arg Leu Ala Tyr Asn Thr Gly Gly Gln Val Ser Asn Asn Asn Gln Asn
                340                 345                 350

Ser Asn Thr His Pro Thr Val Gly Val Tyr Asn His Gln Glu Val Leu
                355                 360                 365

Pro Gly Ser Val Trp Met Asp Arg Asp Val Tyr Leu Gln Gly Pro Ile
        370                 375                 380

Trp Ala Lys Ile Pro Glu Thr Gly Ala His Phe His Pro Ser Pro Ala
385                 390                 395                 400

Met Gly Gly Phe Gly Leu Lys His Pro Pro Pro Met Met Leu Ile Lys
                405                 410                 415

Asn Thr Pro Val Pro Ser Asn Val Ala Ala Phe Ser Asp Val Pro Val
            420                 425                 430

Lys Ser Phe Ile Thr Gln Tyr Ser Thr Gly Gln Val Thr Val Glu Ile
            435                 440                 445

Glu Trp Glu Leu Lys Lys Glu Asn Ser Lys Arg Trp Asn Pro Glu Ile
        450                 455                 460

Gln Tyr Thr Asn Asn Tyr Asn Asn Pro Thr Phe Val Asp Phe Ala Pro
465                 470                 475                 480

Asp Thr Ser Gly Glu Tyr Arg Thr Thr Arg Ala Ile Gly Thr Arg Tyr
                485                 490                 495

Leu Thr Arg Pro Leu
                500
```

US 8,420,372 B2

PORCINE ADENO-ASSOCIATED VIRUSES

PRIOR APPLICATION INFORMATION

The instant application claims the benefit of U.S. Provisional Patent Application 60/969,733, filed Sep. 4, 2007.

BACKGROUND OF THE INVENTION

Adeno-associated viruses (AAV) are non-enveloped, non-pathogenic viruses with a single-stranded genome approximately 4.7 kb in length of either positive or negative polarity. The replication of AAV necessitates a coinfection with helper virus such as Adenovirus or Herpes Simplex virus. In the absence of helper virus, AAV integrates into the host chromosome to establish a latent infection. AAV has been isolated from many organisms including human, nonhuman primates, ovine, avian, snake, bovine, murine, and caprine (1-13). It has been reported that various AAV serotypes have differing tropisms and can transduce specific organs more efficiently than others, such as the high transduction efficiency of AAV5 in airway epithelial, muscle, and retina cells as compared to AAV2 (14, 15).

Gene transfer vectors derived from AAV can deliver genes in a variety of tissues in vivo. Recent observations have also promoted the evaluation of AAV as potential genetic vaccine vectors due to their long-term expression profile which can stimulate robust antibody responses (16, 17). Currently, clinical trials are taking place using AAV as a vector for the treatment of ailments such as Parkinson's disease, Cystic fibrosis, Leber's congenital amaurosis, HIV infection, and various other genetic disorders (18, 19, 20, 21). These recombinant AAV (rAAV) vectors are based on the well characterized human AAV serotype 2 which is seroprevalent in up to 80% of the human population with neutralising antibodies found in 35% of them (22).

The AAV capsid proteins encoded by the cap gene were shown to be the main determinant for tissue tropism and constitute an important target for the immune response. The cap gene encodes three proteins expressed from two different alternatively spliced transcripts; VP1, VP2, and VP3. Some serotypes of AAV were found to be less immunogenic than others which may translate into better gene transfer vehicle and less efficient vaccine vector or vice versa (23, 24, 25). In the past, AAV has conventionally been isolated from contaminated adenoviral stocks or young, sick animals or children (1, 2, 3, 4, 5, 6, 7, 9, 12). Recently, isolation of new AAV isolates was extensively performed using PCR amplification of AAV sequences from genomic DNA of different animal species (8, 10, 11, 13). In this study, novel porcine AAV sequences were identified by PCR using genome walking strategies. We describe the isolation of novel AAVpo1 and the characterisation of the serological profile and tissue tropism in vitro and in vivo.

Adeno-associated virus (AAV) is a non-pathogenic parvovirus with a single-stranded DNA genome. The virus typically has a relatively small genome size.

While other parvoviruses replicate autonomously, wild type AAV requires co-infection with a helper virus for lytic phase reproduction. In the absence of a helper virus, wild-type AAV establishes a latent, non-productive infection with long-term persistence.

SUMMARY OF THE INVENTION

According to a first aspect of the invention, there is provided a method for the preparation of a recombinant porcine AAV particle comprising:

providing a cell engineered to express:
- a peptide having at least 80% identity to a porcine AAV capsid protein selected from the group consisting of VP1, VP2 and VP3;
- a functional rep gene;
- a minigene comprising two AAV inverted terminal repeats and a transgene inserted between the two inverted terminal repeats; and
- sufficient helper functions to permit packaging of the minigene into a porcine AAV capsid particle.

According to a second aspect of the invention, there is provided a single dose, injectable pharmaceutical composition comprising $1 \times 10^9$-$1 \times 10^{13}$ purified recombinant AAV particles prepared according to the method of claim 1 and a suitable excipient.

BRIEF DESCRIPTION OF THE DRAWINGS AND TABLES

FIG. 1. Phylogenetic tree representing alignments of known AAV serotypes with novel porcine AAVs. Alignments were performed based on the truncated regions of known AAV serotypes corresponding to those regions of the AAV genomes isolated from porcine tissues. The 1.7 kb rep-cap sequence was isolated for AAVpo1. The 1.4 kb sequence was found for AAVpo1, AAVpo2, and AAVpo3. A. Left phylogenetic tree of 1.7 kb truncated regions of known AAV serotypes aligned with the isolated 1.7 kb region for AAVpo1 and right phylogenetic tree of truncated 1.4 kb "end-of-cap" region for published AAV serotypes aligned with the novel AAVpo1, -po2, and -po3 1.4 kb regions. B. Figure depicting the full-length AAV genome. The AAV genome is composed of a rep gene and a cap gene flanked by ITRs on either side. The lines for the 1.7 kb rep-cap region and 1.4 end-of-cap region represent the regions of the AAV genome isolated for AAVpo1, -po2, and -po3, as well as the regions of published AAV serotypes used for alignment.

FIG. 2. Western blot of A. AAV2/5 capsid proteins and B. AAV2/po1 VP1, VP2, and VP3 using AAV VP1, VP2, VP3 monoclonal antibodies. AAV2/5 VP1 has a predicted molecular weight of 80.42 kDa while AAV2/po1 VP1 has a predicted weight of 80.18 kDa using DNASTAR Lasergene 7 Protean software. Proteins were isolated from transfected HEK 293T cells and separated by a 10% SDS PAGE, and subsequently transferred to nitrocellulose paper. Mouse monoclonal anti-VP1, -VP2, and -VP3 were used as the primary antibody and goat anti-mouse horseradish peroxidase (HRP) conjugated antibody as secondary antibody.

FIG. 3. Electron microscopy of chimeric AAV2/5 and AAV2/po1 CsCl-purified particles containing the LacZ transgene at 100,000× magnification. Particles were produced by transfection of subconfluent HEK 293T cells and purified 48 hours later.

Figure 4:
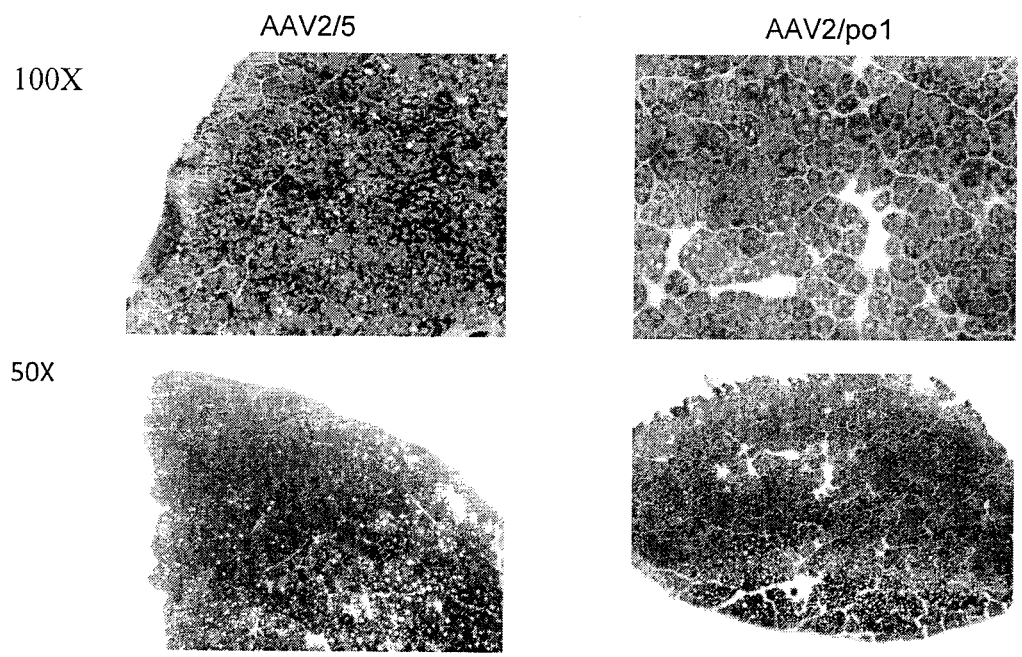

FIG. 4. Muscle susceptibility to AAV2/5 or AAV2/po1 following intramuscular injection in BALB/c mice. The mice were sacrificed and muscle was harvested 30 days p.i., frozen with OCT., and sections were cut using a cryostat.

Figure 5:
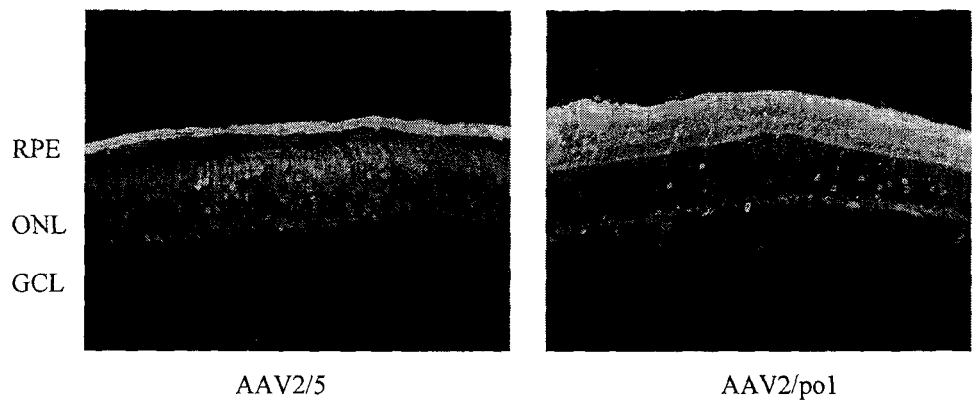

FIG. 5. AAV2/po1 or AAV2/5 transduction following subretinal injection in C57BL/6 mice. EGFP was used as a reporter gene. The retinal cell layers are of the eyecup depicting the RPE (retinal pigment epithelium), ONL (photoreceptor outer nuclear layer), and the GCL (ganglion cell layer).

FIG. 6. Nucleotide sequence of AAVpo1a Rep/Cap 1643 bp (SEQ ID No. 18).

FIG. 7. Nucleotide sequence of AAVpo1b End of Cap 1398 bp (SEQ ID No. 19).

FIG. 8. Nucleotide sequence of AAVpo1c Full Cap 2151 bp (SEQ ID No. 20).

FIG. 9. Nucleotide sequences of AAVpo2 End of Cap 1385 bp (SEQ ID No. 21) and AAVpo3a Signature Sequence 252 bp (SEQ ID No. 22).

FIG. 10. Nucleotide sequence of AAVpo3b End of Cap 1549 bp (SEQ ID No. 23).

FIG. 11. Amino acid sequences of AAVpo1 VP1 Peptide (SEQ ID No. 24), AAVpo1 VP2 Peptide (SEQ ID No. 25) and AAVpo1 VP3 Peptide (SEQ ID No. 26).

Table 1. Primer names and primer sequences used to isolate novel AAV sequences from various porcine tissues.

Table 2: Nucleotide and amino acid identity of AAVpo1 VP1 capsid with other known AAV serotypes.

Table 3: Tropism of AAV2/po1 or AAV2/5 in different cell lines.

Table 4: Biodistribution of AAV2/5 and AAV2/po1 after IV Tail Vein injection in mice.

Table 5: Neutralisation profile of homologous or heterologous AAV2/po1 or AAV2/5 anti-serum.

Table 6: Neutralisation of AAV2/po1 or AAV2/5 by pooled Human Ig (Immune Globulin Intravenous (Human) Carimune® NF).

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is the discovery of a number of novel porcine adeno-associated viruses and nucleotide and amino acid sequences associated therewith. As will be appreciated by one of skill in the art and as discussed below, these sequences can be used advantageously in the generation of delivery constructs, for example, for the delivery of an antisense agent, a gene therapy agent or a vaccine agent.

It is noted that high antigenic compatibility and low toxicity is associated with xenograft transplantation of porcine tissues in immunodeficient human recipients. We hypothesized that AAVs of porcine origin, if existing, could be highly compatible to human tissues and of high efficiency for in vivo gene transfer. Porcine tissues were screened for the presence of AAV using universal primers designed from an alignment of published AAV sequences. In total, AAV sequences were detected in 9 out of 21 farmed pigs. Several AAV sequences were isolated from various porcine tissues, and BLAST analysis confirmed high to low homology with known AAV sequences of different origin. Sequence analysis confirmed the isolation of at least three novel porcine AAV isolates which we named AAVpo1, -po2, and -po3 (see FIGS. 6-11). The AAVpo1 capsid protein was closely related to AAV5 capsid with 87.1% amino acid identity. AAVpo2 was found to be related to human AAV2 whereas the isolated sequence of AAVpo3 was highly divergent from all AAV isolates previously described. Hybrid vector particles based on AAV2 rep and AAVpo1 cap with a packaged LacZ transgene were successfully produced. The novel AAV2/po1 could efficiently transduce muscle fibers or the retinal pigment epithelium following intramuscular or subretinal injection in mice respectively. Serological analysis indicates that AAVpo1 is a unique serotype and that pre-existing immunity to AAVpo1 could not be detected in the human sera evaluated. Novel AAVs derived from porcine tissues may significantly contribute to the generation of new preventive or curative clinical modalities acceptable for human use.

As will be appreciated by one of skill in the art, such viruses and the nucleotide sequences thereof can be used in the construction of useful products and reagents, for example, for the production of gene replacement or gene expression vectors.

For example, therapeutic or prophylactic therapies in which the constructs described herein have or are likely to have utility include but are by no means limited to blood disorders, lung disorders, neurological disorders and muscle disorders.

As will be appreciated by one of skill in the art, the genetic factors required for several disease states are known and accordingly constructs may be prepared which either reduce expression, reduce translation or replace such genetic factors. Examples include but are by no means limited to hormones and growth and differentiation factors, including but by no means limited to insulin, glucagons, growth hormone, parathyroid hormone, growth hormone releasing factor, follicle stimulating hormone, luteinizing hormone, cumin chorionic gonadotropin, vascular endothelial growth factor, angiopoietins, angiostatin, granulocyte colony stimulating factor, erythropoietin, connective tissue growth factor, basic fibroblast growth factor, acidic fibroblast growth factor, epidermal growth factor, platelet-derived growth factor, insulin growth factors I and II, any one of the transforming growth factor superfamily, including TGFα, activins, inhibins or any of the bone morphogenic proteins (BMP) BMPs 1-15, any one of the heregluin/neuregulin/ARIA/neu differentiation factor family of growth factors, nerve growth factor, brain-derived neurotrophic factor, neurotrophns NT-3 and NT-4/5, ciliary neurotrophic factor, glial cell line derived neurotrophic factor, neurturin, agrin, any one of the family of semaphorins/collapsins, netrin-1 and netrin-2, hepatocyte growth factor, ephrins, noggin, sonic hedgehog, tyrosine hydroxylase and cystic fibrosis transmembrane conductance regulator. Further examples as well as additional information on the construction and use of AAV particles may be found at least in published US Patent Application 2007/0036760 which is incorporated herein by reference, particularly for the sections describing preparation of constructions and use of said constructs.

For example, as can be seen in FIG. 1, AAVpo2 is phylogenetically related to AAV2 and accordingly it is expected that AAVpo2 may have similar properties, that is, expression in skeletal muscles, neurons, vascular smooth muscle cells and hepatocytes.

Similarly, AAVpo1 is related to AAV5 and accordingly is expected to have similar properties. However, AAVpo1 is functionally different than AAV5 and transduces less cell types, as discussed herein.

As shown in FIG. 1, AAVpo3 is more distantly related to a number of AAV isolates.

As will be appreciated by one of skill in the art, in some embodiments, the 'relatedness' of different clades can be used advantageously when designing or developing a treatment program. For example, as discussed below, ITRs from one clade are likely to be compatible with capsid proteins from other closely related clades. In other embodiments, following an initial treatment with a given clade, a second treatment may be administered using a distantly related clade, thereby reducing the likelihood of cross-reactivity, that is, that the second delivery construct will be recognized by the host's immune system. It is of note that the first and second delivery constructs may carry the same or a similar insert (for example, an antigenic agent for vaccination) or may contain different inserts.

AAV is found in many tissues, including the heart of a high percentage of human and nonhuman primates. Transplantation of pig tissues (eg heart valves) into human has been well documented. During numerous xenotransplantations in immunocompromised individuals, no side effects due to sudden viral replication originating from the transplanted tissue were noted. On the other hand, viruses transmitted by non-human primates are often dangerous pathogens (Ebola etc) and can adapt and become human pathogens (SIV to HIV). Historically this is also a concern (transmission of SV40 from the polio vaccine that was produced in monkey cells.

As will be apparent to one of skill in the art, the capsid is responsible for the tropism and vector entry and thus gene transfer efficacy. Accordingly, in one embodiment of the invention, there is provided a method for the preparation of a recombinant porcine AAV particle comprising:

providing a cell engineered to express:
a peptide having at least 80% identity to a porcine AAV capsid protein selected from the group consisting of vp1, vp2 and vp3;
a minigene comprising two AAV inverted terminal repeats and a transgene inserted between the two inverted terminal repeats;
a functional rep gene compatible with said AAV inverted terminal repeats; and
sufficient helper functions to permit packaging of the minigene into a porcine AAV capsid particle, and
recovering said porcine AAV capsid particle from said cell.

As will be appreciated by one of skill in the art, the cell as described above may be described as a packaging cell. Specifically, the cell may be engineered by means known in the art to express, either constitutively or inducibly, the elements listed above. It is further of note that these expression constructs may be supplied by transient expression constructs or by expression constructs integrated into the genome of the packaging cell. It is further noted that the amino acid sequences of AAVpo1 VP1 (SEQ ID No. 24), VP2 (SEQ ID No. 25) and VP3 (SEQ ID No. 26) are provided in FIG. 11.

As will be appreciated by one of skill in the art, 'porcine AAV capsid protein' refers to porcine-derived AAV virus sequences which encode all or part of at least one of VP1, VP2 or VP3. Attention is directed to FIGS. 6-11 for examples of such sequences and/or sequences from which said VP1, VP2 and VP3 amino acid sequences may be derived (for example, by searching an appropriate nucleotide sequence for a homologous open reading frame).

In some embodiments of the invention, the peptide has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to a procine adeno-associated virus capsid protein selected from the group consisting of VP1, VP2 and VP3. In some embodiments, VP1, VP2 and VP3 are the amino acid sequences of AAVpo1 VP1 (SEQ ID No. 24), VP2 (SEQ ID No. 25) and VP3 (SEQ ID No. 26) respectively.

A peptide having at least 80% identity to a porcine AAV capsid protein may be a porcine AAV capsid protein related to a sequence shown in FIG. 11, or may be a humanized version thereof or a chimeric version of two or more AAV capsid proteins. As will be appreciated by one of skill in the art, such chimeric hybrids may easily be assembled by comparing two or more AAV capsid peptides for regions of high similarity (conserved regions) and regions of lesser similarity (variable regions) and then preparing chimeric capsids by substitution or combination of regions or domains of interest.

It is also important to note that on comparison of VP1, VP2 and VP3 sequences from a variety of adeno-associated viruses, it is possible to determine highly conserved regions of the capsid protein in which alteration, insertion and/or deletion is unlikely to be tolerated. Similarly, variable or non-conserved or less highly conserved regions can be determined in a similar manner which one of skill in the art will understand are more likely to tolerate alteration.

As will be appreciated by one of skill in the art, the transgene is inserted between the two inverted terminal repeats. It is of note that the ITRs and the AAV REP protein must be compatible; however, it is noted that determining such compatibility is well within the skill of one of knowledgeable in the art. It is also important to note that the AAV ITR does not necessarily need to be derived from porcine AAV.

As discussed above, the transgene may be used to correct or ameliorate gene deficiencies or defects which may include deficiencies in which normal genes are expressed at less than normal levels or deficiencies in which the functional gene product in not expressed at all. In other embodiments, the transgene may encode an antisense construct arranged to reduce expression of a specific target or the transgene may encode an antigen or immunogenic domain for use as a vaccine.

While the currently accepted insert or transgene size limit is ~4 kb it is believed that up to 10 kb can be incorporated and transferred although efficacy is lower (about 80%). Above 10 kb, efficiency of transfer starts dropping significantly.

As will be appreciated by one of skill in the art, 'helper functions' include but are by no means limited to sequences capable of inducing AAV expression. It is of note that such sequences are well known to one of skill in the art. In one embodiment, the host cell is provided with and/or contains an E1a gene product, an E1b gene product, an E2a gene product and/or an E4 ORF6 gene product. As will be known to one of skill in the art, the helper virus is primarily required by AAV to drive the cell into "S phase" in order to drive viral DNA replication. While both Adenovirus and HSV have the ability to do this, other means known in the art may also be used within the invention.

It is of note that the host cell or packaging cell may be selected from any suitable biological organism, including prokaryotic and eukaryotic cells, including but by no means limited to insect cells, yeast cells and mammalian cells. In a preferred embodiment, the cells are HEK 293T cells.

As will be appreciated by one of skill in the art, the assembled particles may be recovered from the packaging cell and purified by any suitable means known in the art, for example, by cesium chloride gradient. It is important to note that as used in this context, 'purity' does not require absolute purity but only that the particles have been substantially enriched in concentration or isolated or purified away from cellular components.

In some embodiments, there is provided a single dose, injectable pharmaceutical composition comprising $1 \times 10^9$-$1 \times 10^{13}$ purified recombinant AAV particles and a suitable excipient.

The cap gene can trans-complement AAV chimeric particles with the AAV2 rep gene and produce functional vector capable of achieving gene transfer in different susceptible tissues in vitro and in vivo. The present study reports the isolation of sequences defining three novel AAV isolates isolated from porcine tissues. The complete sequence of the cap gene of the isolate AAVpo1 was used to generate functional particles that showed strong tropism mainly for muscle fibers and the retinal pigment epithelium. Good transduction of muscle fibers combined to poor transduction of other tissues could make AAV2/po1 an attractive gene transfer vehicle for systemic delivery and possibly help the treatment of myopathies such as Duchenne muscular dystrophy. Muscles susceptibility will need to be evaluated in other animal models to further investigate this hypothesis since AAV2/po1, which has also been isolated from porcine liver and lung, may demonstrate a different preferential tropism in other species.

A high histocompatibility has been documented of porcine tissues into human recipients following xenotransplantation. We hypothesized that this compatibility would translate in porcine AAVs with good transduction efficiency and high safety profile for therapeutic applications in humans. An interesting observation is the isolation of AAV2 sequences identical or closely resembling the original sequence of the virus isolated from human tissue. Contamination of samples with exogenous AAVs is always a concern when isolating sequences with a methodology as sensitive as PCR. The complete absence of AAV2 vector in our research institute before the isolation of sequences from genomic pig DNA strongly suggest that the isolation of AAV2 sequences was not the result of contamination but rather present in the porcine tissues extract tested. This may indicate zoonotic transmission and/or co-evolution of certain AAVs in pigs and some humans supporting the concept of high compatibility between the two species. If accurate, this phenomenon may however be of low incidence since AAV2/po1 was not neutralised by the pooled human Ig tested.

The absence of neutralising antibody to AAV2/po1 in pooled human sera adds a desired characteristic for in vivo administration of the vector in humans. The long-term safety profile following porcine-derived AAVs in vivo remains to be investigated. Finally, absence of cross-neutralisation with anti-serum against AAV2/po1 and anti-serum from all other serotypes evaluated strongly suggest that AAVpo1 is a unique serotype and structurally different from the other AAVs evaluated.

The invention will now be further described by way of example; however, the examples do not necessarily limit the invention.

Use of PCR to Determine AAVpo1, -po2, and -po3 Sequences from Porcine Tissues.

Since AAV has the ability to integrate its genome into the host chromosome during a latent infection, we employed the use of PCR techniques to isolate novel AAV sequences from genomic porcine DNA similarly to previous work reported by Gao et al. (8) and Mori et al. (11). Various pig tissues including heart, lung, spleen, liver, and gut were harvested from rural private farms and industrial slaughterhouses, and DNA was isolated and screened for the presence of novel AAV sequences by PCR. The use of primers specific for conserved regions of the AAV genome generated at least three distinct AAV sequences from porcine tissues we called AAVpo1, AAVpo2 and AAVpo3. A 258 bp sequence corresponding to the novel AAVpo1 was found in various organs from nine pigs obtained from three different locations. In contrast, the highly divergent 252 bp and 1.4 kb AAVpo3 sequence was only found in the intestine of one animal. Along with the unique porcine AAV sequences, other sequences highly similar (with 1 to 20 nucleotide changes throughout the cap gene) or identical to AAV2 cap were also isolated from approximately 12.5% of the porcine tissues screened. PCR amplification was also performed to isolate a 1.64 kb sequence which spans the rep and cap genes and a 1.4 kb sequence which overlaps with the 1.64 kb fragment and covers the 3' end of the cap gene (FIG. 1). The entire cap gene of the AAVpo1 could be isolated from 63% of the tissues obtained from privately owned farmed pigs with the spleen having the highest success with 75% of AAV sequence recovery. Porcine lung, heart and liver were second for successful isolation of AAV sequences. Only one farmed-animal proved negative for AAV sequences, while tissue samples originating from the slaughterhouse showed only 4% of AAV sequence recovery from 51 samples.

Alignment of the nucleotide sequence of AAVpo1, -po2, or -po3 with available AAV sequences revealed that AAVpo1 was more closely related to AAVgo.1, AAVpo2 to AAV2, and that AAVpo3 was uniquely divergent from the others (FIG. 1). AAVpo1 cap showed 89.2% amino acid identity and 86.3% nucleotide identity with AAVgo.1 and 87.1% amino acid identity and 84.7% nucleotide identity with AAV5 (Table 2). The predicted amino acid sequences for the capsid proteins of known AAV serotypes when compared to AAVpo1 show that region C, G, and H are the most divergent regions.

Production of AAV2/po1 Hybrid Vector.

Several studies have demonstrated that AAV2 rep can trans complement AAV cap gene resulting in successful production of functional AAV particles with the capsid protein of interest. Triple transfection of the trans packaging plasmid encoding for AAV2 rep and -po1 cap genes, a LacZ expressing cis-plasmid and the helper plasmid containing the adenoviral genes necessary to drive production of AAV in HEK 239T cells resulted in the successful generation of chimeric AAV2/po1 particles (FIGS. 2 and 3). Purification of AAV2/po1 by cesium chloride gradient produced particles showing the distinct pattern of VP1, VP2 and VP3 on a denaturing acrylimide gel visualized by Western blot using anti-VP1, -VP2, and -VP3 antibodies (FIG. 2). Protean software of DNASTAR Lasergene 7 predicted the VP1 protein of AAVpo1 to have 716 amino acids with a molecular weight of 80.18 kDa, and the VP1 protein of AAV5, used as a positive control, to contain 724 amino acids with a predicted molecular weight of 80.42 kDa. Electron microscopy revealed that AAVpo1 particles were comparable in shape and size to AAV2/5 with a diameter of 20-25 nm (FIG. 3). Viral titres of 0.4 to $4\times10^{13}$ total GC of AAVpo1 per preparation of 3 to 4 ml could routinely be obtained as assessed by Taqman PCR.

Transduction Efficiency of AAV2/po1 in Cultured Cells.

Transduction efficiency was evaluated for AAV2/po1 on different cell types in vitro. The closely related AAV2/5 vector was also evaluated in parallel and used as a benchmark. Subconfluent cell lines from different species including mouse (NIH 3T3), dog (MDCK), pig (VirBle1), monkey (VeroE6) and human (HEK 293T and HeLa) were infected with $1\times10^9$ GC of each AAV expressing LacZ and the number of positive blue cells recorded after 48 hours. Results, summarized in Table 3, show that AAV2/po1 transduced all the cultured cell lines tested less efficiently than AAV2/5, with the exception of Vero E6 and VirBle1 cells. VirBle1 is a porcine retinal cell line which showed substantially higher susceptibility to AAV2/po1 than AAV2/5.

Tropism of AAV2/po1 in Mice.

The tropism and transduction efficiency of AAV2/po1 was studied in mice in parallel to AAV2/5 that was used as a control. $1\times10^{11}$ GC was administered per mouse in the muscle, liver or lung by intramuscular, tail vein or intranasal injection and were harvested and analysed 30 (liver and muscle) or 60 (lung) days after administration. LacZ positive cells could not be detected in AAV2/po1-treated lungs and only rare scattered positive cells were observed in the liver (only anecdotal cells could be detected per 20 liver sections). In contrast, high transduction efficiency was observed in the muscle following I.M. injection of AAV2/po1 which was comparable to that observed with AAV2/5 in the same conditions (FIG. 4). Subretinal injections of AAV2/po1 also resulted in high transduction efficiency of the retinal pigment epithelium and photoreceptor layers again comparable to the efficiency recorded for AAV2/5 (FIG. 5). Cells in the inner nuclear layer and some cells morphologically similar to Muller Cells were also transduced following AAV2/po1 administration.

Biodistribution of AAV2/po1 was also evaluated in mice from various organs 30 days after systemic administration by tail vein injection (Table 4). Results showed that AAV GC numbers, established from the copy number of the LacZ gene per cell, were significantly lower for AAV2/po1 than for AAV2/5 in all organs studied with the exception of the muscle.

Serological Profile of AAV2/po1.

Neutralisation assays were performed with the antisera collected from AAV2/po1 and AAV2/5 intramuscularly injected mice in order to evaluate cross-neutralisation between the two related isolates. Antiserum from AAV2/po1 or AAV2/5 treated mice had neutralising antibody titer of 1:1280 or 1:5120 against themselves respectively (Table 5). In contrast, AAV2/po1 antiserum had undetectable neutralising antibody against AAV2/5 and vice versa. Overall, AAV2/po1 was not neutralised by serum collected from mice exposed to AAV2/2, -2/3, -2/4, -2/5, -2/6, -2/7 or -2/8 vector. The AAV2/po1 and AAV2/5 expressing LacZ were also incubated with pooled Human Ig at various dilutions to address the serosusceptibility of the vectors to antibody found in humans. At least fifty percent of AAV2/5 particles were neutralised with $7.5 \times 10^{-5}$ mg/mL of pooled human Ig while neutralisation was not detected for AAV2/po1 with undiluted human Ig at 12 mg/ml (Table 6).

Isolation of Genomic DNA from Porcine Tissues and Amplification of AAV Sequences.

Various porcine tissues including the lung, heart, spleen, gut, and liver were screened for the presence of AAV sequences. Porcine tissue samples were collected from various locations such as industrial slaughterhouses and private rural farms. Genomic DNA was isolated from approximately 25 mg of each tissue using QIAamp® DNA Mini Kit (QIAGEN). Primers SIG+ and SIG– (5'-GGTAATTC-CTCGGGAAATTGGCATT-3' (SEQ ID No. 3) and 5'-GAATCCCCAGTTGTTGTTGATGAGTC-3' (SEQ ID No. 2) respectively) were used to PCR amplify short fragments referred as the "signature region" as previously described by Gao et al. (8). These fragments of 252 and 258 by corresponded to two novel AAV sequences from porcine tissues generating AAVpo1 and -po3 fragments. BLAST analysis showed that AAVpo1 and -po3 sequences were significantly different from previously described AAV sequences available on GenBank. The 5' sequence of cap was isolated with the primer RC+ described by Mori et al. (11); 5'-GGTGCGTAAACTGGACCAATGAGAAC-3' (SEQ ID No. 1) and the primer SIG– generating a 1.64 kb fragment encompassing the end of the rep gene and beginning of cap region. To isolate the 3' end of the cap gene, three successive primers were generated based on conserved regions of the AAV genome along with a reverse degenerate primer in a three step nested thermal-asymmetric interlaced (TAIL) PCR. The three successive primers are: PAAVSP1+ (5'-GGA-RATTGGCATTGCGATTCC-3' (SEQ ID No. 8)), PAAVSP2+ (5'-GACTTCAACCGCTTCCACAGCCAC-3' (SEQ ID No. 9)), and PAAVSP3+ (5'-GACTCATCAA-CAACCWACTGGGG-3' (SEQ ID No. 4)). The sequence of the degenerate primer CED– is: 5'-ACTGAMACGAAT(H/–)AMMCGGTTTATTGA-3' (SEQ ID No. 5). A 1.4 kb fragment which overlapped with the 1.64 kb 5' end sequence was isolated using these primers. Specific primers were also designed to isolate the full length cap gene from porcine tissues in one PCR with the following sequences: PO1CAPBEGIN+ (5'-ATGTAGTGGATCTTGACGATG-3' (SEQ ID No. 6)) and PO1CAPEND– (5'-CATGTGACAG-GATAGGGTTA-3' (SEQ ID No. 7)). All PCR amplified fragments were gel purified using QIAquick® Gel Extraction Kit (QIAGEN) and subsequently cloned into pCR®2.1-TOPO® Vector (Invitrogen). DNA sequencing was performed by the DNA Core Facility at the National Microbiology Laboratory.

Production of Hybrid AAV2/po1 Particles.

Chimeric AAV particles were produced with AAV2 rep and AAVpo1 cap expressing plasmids. AAVpo1 cap was cloned in place of the AAV cap gene in the packaging plasmid p600 trans using SwaI and NotI restriction sites, generating pACK 2/po1. The AAV2CMVLacZ or EGFP plasmids (26) expressing the LacZ or EGFP reporter genes from a CMV promoter were used as the cis-plasmid containing the recombinant AAV genome. Triple transfection of Human Embryonic Kidney 293T (HEK 293T) cells with AAV2CMVLacZ or EGFP, the packaging plasmids pACK2/po1 or pACK2/5 (29) and the helper plasmid pDELTA F6 containing adenoviral genes necessary to drive AAV replication was performed with $CaPO_4$ as described previously (27, 28). Recombinant AAV vectors were all purified by $CsCl_2$ gradients as previously described (28). Titres of AAV vector preparations were determined by TaqMan® PCR for genome copy (GC) with primers LACZ+ (5'-TTAACCCGCCATGCTACTTATCTA-3' (SEQ ID No. 15)), LACZ– (5'-TGAACTAATGACCCCGTAATTGATT-3' (SEQ ID No. 16)), and probe LACZP (5'-CTCTAGGAA-GATCGGAATTCGCCCTTAAGCTAG-3' (SEQ ID No. 17)) or with primers for the bGH poly A as previously described (26). The number of transducing particles per GC was also determined for AAV2/po1 and AAV2/5 on HEK 293T cells (on average, for every $1 \times 10^9$ GC, AAV2/po1 and AAV2/5 had $2 \times 10^5$ and $4 \times 10^5$ transducing units (TU) respectively). The AAV2/5-CMVEGFP and AAVpo1-CMVEGFP were produced by the Telethon Institute of Genetics and Medicine (TIGEM) AAV vector core. AAV specimens were prepared for electron microscopy by adsorption to glow discharged carbon coated formvar films on 400 mesh copper grids for one minute, and negatively contrasted with 2% methylamine tungstate (Nanoprobes, Yaphank, N.Y.). Specimens were imaged in a FEI Tecnai 20 transmission electron microscope operating at 200 kV, at a nominal instrument magnification of 200000×. Digital images of the specimens were acquired by an AMT Advantage XR 12 CCD camera (AMT, Danvers, Mass.).

Serology and Neutralisation Assay.

Recombinant AAV2/5 and AAV2/po1 vectors containing the LacZ transgene were injected intramuscularly into BALB/c mice ($1 \times 10^{11}$ GC per injection) in the left tibialis anterior. Serum samples were collected 28 days post infection for serology analysis. The sera were inactivated at 56° C. for 45 minutes. Serial dilutions of each sample (1:10, 1:20, 1:40, etc, in 50 μl of DMEM) was mixed with equal volume of the appropriate AAV encoding the LacZ reporter gene (80-100 transducing units/well) and incubated at 37° C. for 60 minutes. The mixture was then transferred onto subconfluent HEK 293T cells in 96-well flat-bottomed plates and incubated for 90 minutes at 37° C. in 5% $CO_2$. Control wells were infected with equal amount of AAV vector without the addition of serum or with the addition of non-immune serum. 100 μl of DMEM supplemented with 20% FBS was then added to each well and the plates were incubated at 37° C. in 5% $CO_2$ for 48 hours. Cells were subsequently stained with 5-bromo- 4-chloro-3-indolyl β-D-galactoside (X-gal) and examined under a microscope. The same type of neutralisation assay was also performed with Immune Globulin Intravenous Human Carimune® NF (CSL Behring) in place of the sera. Sample dilutions which showed >50% reduction in the number of LacZ positive cells compared to controls scored positive for neutralising antibody.

Histology and Histochemical Staining.

For muscle gene delivery, the tibialis anterior was harvested 30 days after intramuscular injection of mice. The muscle was embedded in O.C.T. medium and snap frozen in liquid nitrogen-cooled isopentane. For lung gene delivery, AAV2/5 or AAV2/po1 vector expressing LacZ was administered intranasally in BALB/C mice at $1 \times 10^{11}$ GC/mouse in 50 μl. The lungs and trachea were harvested and inflated with a 1:1 solution of PBS and O.C.T. medium 64 days post-administration and embedded in O.C.T. medium. For liver gene transfer, each mouse was injected in the tail vein with $1 \times 10^{11}$ GC in 100 μl and the liver was harvested 30 days later and embedded in O.C.T. medium. Lung, trachea and liver samples were frozen on ethanol-cooled dry ice. For all tissues, 10 μm thick sections were cut with a cryostat and fixed with 1.6% glutaraldehyde. The sections were then incubated overnight with X-gal at 37° C., lightly stained with eosin and dehydrated in 70-100% ethanol solutions. Sections were analysed on a light microscope.

Subretinal Injections and Retinal Transduction Assessment.

All procedures on animals were performed in accordance with institutional guidelines of the ARVO Statement for the Use of Animals in Ophthalmic and Vision Research. Four-week-old male C57BL/6 mice (Harlan) were used for injections of rAAV vector Before vector administration, mice were anesthetized with an intraperitoneal injection of avertin (1.25% [wt/vol] 2,2,2-tribromoethanol and 2.5% [vol/vol] 2-methyl-2-butanol [Sigma-Aldrich]) at 2 ml/100 g of body weight. Subretinal vector administrations were performed as described previously using 1 ul of a vector solution containing $1 \times 10^{12}$ GC/ml. A month after vector administration, mice were sacrificed and their eyeballs were harvested and fixed overnight by immersion in 4% paraformaldehyde. The eyeballs were cut so that the lens and vitreous could be removed, leaving the eyecup. Mice eyecups were infiltrated with 30% sucrose for cryopreservation and were embedded in tissue-freezing medium (O.C.T. matrix; Kaltek). For each eye, 150 to 200 serial sections (10 μm thick) were cut along the horizontal meridian, and the sections were progressively distributed on 10 slides so that each slide contained 15 to 20 sections representative of the whole eye at different levels. The sections were mounted with Vectashield (Vector Laboratories, Inc.), and retinal histology images were obtained with an Axiocam (Carl Zeiss) at 20× magnification.

Biodistribution in Mice.

AAV2/5 or AAV2/po1 expressing LacZ was administered at $1 \times 10^{11}$ GC in 100 μl PBS per C57BL/6 or BALB/c mouse by IV tail vein injection. Various organs including the heart, liver, spleen, kidney, lungs, small intestine, large intestine, muscle, and pancreas were collected 28 days post-injection and analysed by TaqMan® analysis for the amount of rAAV GC per cell. Briefly, DNA was extracted from approximately 25 mg of each tissue sample with QIAamp® DNA Mini Kit and TaqMan® amplification was performed as described previously (30) with the primers LACZ+, LACZ− and probe LACZP described above. The signal was considered positive when the number of GC was superior to 3 times the number obtained from PBS-injected control tissues. The number of transduced rAAV genomes in each organ is reported as number of GC/cell (500 ng DNA contained within $1.5 \times 10^4$ cells).

While the preferred embodiments of the invention have been described above, it will be recognized and understood that various modifications may be made therein, and the appended claims are intended to cover all such modifications which may fall within the spirit and scope of the invention.

REFERENCES

1. Atchison, R. W., Castro, B. C. & Hamman W. M. (1965) *Science* 149, 754-756.
2. Yates, V. J., el-Mishad, A. M., McCormick, K. J. & Trentin, J. J. (1973) *Infect. Immun.* 7, 973-980.
3. Myrup, A. C., Mohanty, S. B. & Hetrick, F. M. (1976) *Am. J. Vet. Res.* 37, 907-910.
4. Coria, M. F. & Lehmkuhl, H. D. (1978) *Am. J. Vet. Res.* 39, 1904-1906.
5. Clarke, J. K., McFerran, J. B., McKillop, E. R. & Curran, W. L. (1979) *Arch. Virol.* 60, 171-176.
6. Bantel-Schaal, U. & zur Hausen, H. (1984) *Virology* 134, 52-63.
7. Rutledge, E. A., Halbert, C. L. & Russell, D. W. (1998) *J. Virol.* 72, 309-319.
8. Gao, G. P., Alvira, M. R., Wang, L., Calcedo, R., Johnston, J. & Wilson, J. M. (2002) *Proc. Natl. Acad. Sci. USA* 99, 11854-11859.
9. Farkus, S. L., Zadori, Z., Benko, M., Essbauer, S., Harrach, B. & Tijssen, P. (2004) *J. Gen. Virol.* 85, 555-561.
10. Gao, G., Vandenberghe, L. H., Alvira, M. R., Lu, Y., Calcedo, R., Zhou, X. & Wilson, J. M. (2004) *J. Virol.* 78, 6381-6388.
11. Mori, S., Wang, L., Takeuchi, T. & Kanda, T. (2004) *Virology* 330, 375-383.
12. Olsen, E. J., Haskell, S. R., Frank, R. K., Lehmkuhl, H. D., Hobbs, L. A., Warg, J. V., Landgrat, J. G. & Wunschmann, A. (2004) *J. Vet. Diag. Invest.* 16, 461-464.
13. Lochrie, M. A., Tatsuno, G. P., Arbetman, A. E., Jones, K., Pater, C., Smith, P. H., McDonnell, J. W., Zhou, S. Z., Kachi, S., Kachi, M., Campochiaro, P. A., Pierce, G. F. & Colosi, P. (2006) *Virology* 353, 68-82.
14. Davidson, B. L., Stein, C. S., Heth, J. A., Martins, I., Kotin, R. M., Derksen, T. A., Zabner, J., Ghodsi, A. & Chiorini, J. A. (2000) *Proc. Natl. Acad. Sci. USA* 97, 3428-3432.
15. Zabner, J., Seiler, M., Walters, R., Kotin, R. M., Fulgeras, W., Davidson, B. L. & Chiorini, J. A. (2000) *J. Virol.* 74, 3852-3858.
16. Lai, C. M., Shen, W. Y., Brankov M., Lai Y. K. Y., Barnett N. L., Lee S. Y., Yeo I. W. S., Mathur R., Ho J. E. S., Pineda P., Barathi A., Ang C. L., Constable I. J. & Rakoczy, E. P. (2005) *Mol. Ther.* 12, 659-668.
17. Rivera, V. M., Gao, G. P., Grant, R. L., Schnell, M. A., Zoltick, P. W., Rozamus, L. W., Clackson, T. and Wilson, J. M. (2005) *Blood* 105, 1424-1430.
18. Carter, B. J. (2005) *Human Gene Therapy* 16, 541-550.
19. Kaplitt, M. G., Felgin A., Tang, C., Fitzsimons, H.L., Mattis, P., Lawlor, P.A., Bland, R. J., Young, D., Strybin, K., Eidelberg, D. and During, M. J. (2007) *The Lancet* 369, 2097-2105.
20. Moss, R. B., Milla, C., Colombo, J., Accurso, F., Zeitlin, P. L., Clancy, J. P., Spencer, L. T., Pilewski, J., Waltz, D. A., Dorkin, H. L., Ferkol, T., Pian, M., Ramsey, B., Carter, B. J., Martin, D. B. & Heald, A. E. (2007) *Human Gene Therapy* 18, 726-732.
21. Buch, P. K. & Bainbridge, J. W. (2008) *Gene Therapy* 15, 849-857.

22. Chirmule, N., Propert, K. J., Magosin, S. A., Qian, Y., Qian, R. And Wilson, J. M. (1999) *Gene Therapy* 6, 1574-1583.
23. Wang, Z., Blankinship, M. J., Gregorevic, P., Little, M., T., Storb, R. J., Allen, J. M., Tapscott, S. J., Chamberlain, J. S. & Kuhr, C. S. (2005) *Molecular Therapy* 11, S307.
24. Manno, C. S., Pierce, G. F., Arruda, V. R., Glader, B., Ragni, M., Rasko, J. J. E., Ozelo, M. C., Hoots, K., Blatt, P., Konkle, B., Dake, M., Kaye, R., Razavi, M., Zajko, A., Zehnder, J., Rustagi, P., Nakai, H., Chew, A., Leonard, D., Wright, J. F., Lessard, R. R., Sommer, J. M., Tigges, M., Sabatino, D., Luk, A., Jiang, H., Mingozzi, F., Couto, L., Ertl, H. C., High, K. A. & Kay, M. A. (2006) Nature Medicine 12, 342-347.
25. Vandenberghe, L. H., Wang, L., Somanathan, S., Zhi, Y., Figueredo, J., Calcedo, R., Sanmiguel, J., Desai, R. A., Chen, C. S., Johnston, J., Grant, R. L., Gao, G. & Wilson, J. M. (2006) Nature Medicine 12, 967-971.
26. Auricchio, A., Hildinger, M., O'Connor, E., Gao, G. & Wilson, J. M. (2001) Hum. Gene Ther. 12, 71-76.
27. Graham, F. L. & van der Eb, A. J. (1973) Virology 52, 456-467
28. Xiao, X., Li, J. & Samulski, R. J. (1998) J. Virol. 72, 2224-2232.
29. Hildinger, M., Auricchio, A., Gao, G., Wang, L., Chirmule, N. & Wilson, J. M. (2001) J. Virol. 75, 6199-6203.
30. Holland, P. M., Abramson, R. D., Watson, R. & Gelfand, D. H. (1991) Proc. Natl. Acad. Sci. U.S.A. 88, 7276-7280.

TABLE 1

Primer names and primer sequences used to isolate novel AAV sequences from various porcine tissues.

| Primer Name | Primer Sequence |
|---|---|
| 1. CP3 | 5'-GGTGCGTAAACTGGACCAATGAGAAC-3' (SEQ ID NO. 1) |
| 2. Sig3072+ | 5'-GAATCCCCAGTTGTTGTTGATGAGTC-3' (SEQ ID NO. 2) |
| 3. Sig2839- | 5'-GGTAATTCCTCGGGAAATTGGCATT-3' (SEQ ID NO. 3) |
| 4. Cap3158+ | 5'-GACTCATCAACAACWACTGGGG-3' (SEQ ID NO. 4) |
| 5. CapEndDeg- | 5'-ACTGAMACGAATHAMMCGGTTTATTGA-3' (SEQ ID NO. 5) |
| 6. P5LCapBeg+ | 5'-ATGTAGTGGATCTTGACGATG-3' (SEQ ID NO. 6) |
| 7. P5LCapEnd- | 5'-CATGTGACAGGATAGGGTTA-3' (SEQ ID NO. 7) |
| 8. AlexGP+ | 5'-GGARATTGGCATTGCGATTCC-3' (SEQ ID NO. 8) |
| 9. PigSpfor+ | 5'-GACTTCAACCGCTTCCACAGCCAC-3' (SEQ ID NO. 9) |
| 10. ITR5+ | 5'-TTGGCCACTCCCTCTMGCGC-3' (SEQ ID NO. 10) |
| 11. RevRep1397- | 5'-ACGCASCCGTAAAAGGGCAC-3' (SEQ ID NO. 11) |
| 12. ITR3- | 5'-TTTGSCCACTCCCTCTMTGCGC-3' (SEQ ID NO. 12) |
| 13. EndCapSeq+ | 5'-CGTGGACTTTGCTCCAGAC-3' (SEQ ID NO. 13) |

TABLE 1-continued

Primer names and primer sequences used to isolate novel AAV sequences from various porcine tissues.

| Primer Name | Primer Sequence |
|---|---|
| 14. AAVpo3 p | 5'-CAGTCTCGGGGTGAGAAATG-3' (SEQ ID NO. 14) |

TABLE 2

Nucleotide and amino acid identity of AAVpo1 VP1 capsid with other known AAV serotypes.

| | AAVpo1 | |
|---|---|---|
| | % nucleotide identity[1] | % amino acid identity |
| AAV1 | 64.7 | 59.0 |
| AAV2 | 64.2 | 59.5 |
| AAV3 | 63.7 | 59.6 |
| AAV3b | 63.7 | 59.7 |
| AAV4 | 61.5 | 53.6 |
| AAV5 | 84.7 | 87.1 |
| AAV6 | 64.4 | 58.7 |
| AAV7 | 64.6 | 59.2 |
| AAV8 | 66.1 | 59.0 |
| AAV9 | 64.4 | 56.8 |
| AAV10 | 65.2 | 58.8 |
| AAV11 | 61.0 | 54.6 |
| AAV12 | 60.3 | 53.7 |
| AAVgo.1 | 86.3 | 89.2 |
| BAAV | 62.1 | 57.1 |

[1]Alignments were performed using the CLUSTAL W method of MegAlign software (DNASTAR Lasergene 7).

TABLE 3

Tropism of AAV2/po1 or AAV2/5 in different cell lines.

| | AAV2/po1 | AAV2/5 |
|---|---|---|
| RAW | <1 | $6.7 \times 10^1$ |
| NIH 3T3 | <1 | $4.7 \times 10^2$ |
| Vero E6 | $8.7 \times 10^2$ | $2.6 \times 10^2$ |
| MDCK | $6.7 \times 10^2$ | $1.3 \times 10^3$ |
| HeLa | <1 | $1.7 \times 10^3$ |
| 293 | $2.6 \times 10^2$ | $2.3 \times 10^3$ |
| A549 | <1 | $1 \times 10^2$ |
| HepB2 | 5 | $1.9 \times 10^2$ |
| CaCo | <1 | $3.8 \times 10^2$ |
| VirBle1 | $3.6 \times 10^4$ | $1.2 \times 10^3$ |

Values in table represent the number of transduced cells per $1 \times 10^9$ GC of vector.

TABLE 4

Biodistribution of AAV2/5 and AAV2/po1 after IV Tail Vein injection in mice.

| | AAV2/po1 | AAV2/5 |
|---|---|---|
| Heart | 0.004 ± 0.002 | 0.042 ± 0.052 |
| Liver | 0.003 ± 0.003 | 0.186 ± 0.265 |
| Large Intestine | 0.010 ± 0.008 | 0.158 ± 0.133 |
| Small Intestine | 0.004 ± 0.006 | 0.019 ± 0.012 |
| Lung | 0.035 ± 0.004 | 0.955 ± 1.406 |
| Kidney | 0.009 ± 0.009 | 0.171 ± 0.284 |
| Spleen | 0.208 ± 0.339 | 1.774 ± 1.592 |
| Pancreas | 0.004 ± 0.007 | 0.030 ± 0.029 |
| Muscle | 0.080 ± 0.138 | 0.041 ± 0.027 | rAAV genomes LacZ were targeted for TaqMan PCR. Values present the number of genome copies present per cell.

TABLE 5

Neutralisation profile of homologous or heterologous AAV2/po1 or AAV2/5 anti-serum.

| Anti-sera | Vector | |
|---|---|---|
| | AAV2/po1 | AAV2/5 |
| AAV2/po1 | 1:1280 | <1:20 |
| AAV2/5 | <1:20 | 1:5120 |

Values reported represent the dilution of anti-sera required to neutralise >50% of AAV-LacZ particles.

TABLE 6

Neutralisation of AAV2/po1 or AAV2/5 by pooled Human Ig (Immune Globulin Intravenous (Human) Carimune ® NF).

| Vector | Pooled Human Ig (mg/mL) |
|---|---|
| AAV2/po1 | >12 |
| AAV2/5 | $7.5 \times 10^{-5}$ |

Values represent the concentration of the pooled Human Ig required to neutralise >50% of AAV-LacZ particles.

The invention claimed is:

1. A method for the preparation of a recombinant porcine adeno-associated virus (AAV) particle comprising:
providing a cell engineered to express:
porcine AAV capsid protein VP1 consisting of the amino acid sequence as set forth in SEQ ID NO:24;
porcine AAV capsid protein VP2 consisting of the amino acid sequence as set forth in SEQ ID NO: 25;
porcine AAV capsid protein VP3 consisting of the amino acid sequence as set forth in SEQ ID NO:26;
a minigene comprising two AAV inverted terminal repeats and a transgene inserted between the two inverted terminal repeats; and
a functional rep gene compatible with said AAV inverted terminal repeats;
sufficient helper functions to permit packaging of the minigene into a porcine AAV capsid particle; and
recovering said recombinant particle from said cell.

2. A single dose, injectable pharmaceutical composition comprising $1\times10^9$-$1\times10^{13}$ purified recombinant AAV particles prepared according to the method of claim 1 and a suitable excipient.

* * * * *